United States Patent
Robertson et al.

(10) Patent No.: US 8,115,618 B2
(45) Date of Patent: Feb. 14, 2012

(54) RFID ANTENNA FOR IN-BODY DEVICE

(75) Inventors: Timothy L. Robertson, Belmont, CA (US); Olivier Colliou, Los Gatos, CA (US); Eric J. Snyder, South San Francisco, CA (US); Mark J. Zdeblick, Portola Valley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 734 days.

(21) Appl. No.: 12/126,798

(22) Filed: May 23, 2008

(65) Prior Publication Data

US 2008/0316020 A1 Dec. 25, 2008

Related U.S. Application Data

(60) Provisional application No. 60/940,063, filed on May 24, 2007.

(51) Int. Cl.
*G08B 1/08* (2006.01)

(52) U.S. Cl. .................... 340/539.12; 340/573.1

(58) Field of Classification Search ........ 340/10.1–10.6, 340/572.1–572.9, 500, 531, 539.1, 539.11–539.12, 340/573.1; 235/375–385
See application file for complete search history.

(56) References Cited

U.S. PATENT DOCUMENTS

| | | | |
|---|---|---|---|
| 3,607,788 A | 9/1971 | Adolph | |
| 3,642,008 A | 2/1972 | Bolduc | |
| 3,679,480 A | 7/1972 | Brown et al. | |
| 3,719,183 A | 3/1973 | Schwartz | |
| 3,828,766 A | 8/1974 | Krasnow | |
| 3,967,202 A * | 6/1976 | Batz | 342/42 |
| 3,989,050 A | 11/1976 | Buchalter | |
| 4,017,856 A * | 4/1977 | Wiegand | 342/15 |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |

(Continued)

FOREIGN PATENT DOCUMENTS

EP 1246356 10/2002

(Continued)

OTHER PUBLICATIONS

Mackay et al., Radio telemetering from within the body: Inside information is revealed by tiny transmitters that can be swallowed or implanted in man or animal. Science 1961;134(3486):1196-1202.

(Continued)

*Primary Examiner* — Brian A Zimmerman
*Assistant Examiner* — James Yang
(74) *Attorney, Agent, or Firm* — Bozicevic, Field & Francis LLP; Bret E. Field

(57) ABSTRACT

RFID antennas for ingestible devices, such as ingestible event markers, are provided. Aspects of the ingestible devices of the invention include RFID signal transmission antennas with a battery that is activated upon being exposed to fluid in the body. Embodiments of the RFID antennas are configured to emit a detectable signal upon contact with a target physiological site. Also provided are methods of making and using the devices of the invention.

40 Claims, 2 Drawing Sheets

U.S. PATENT DOCUMENTS

| | | | |
|---|---|---|---|
| 4,239,046 A | 12/1980 | Ong | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann et al. | |
| 4,494,950 A | 1/1985 | Fischell | |
| 4,559,950 A | 12/1985 | Vaughan | |
| 4,635,641 A | 1/1987 | Hoffman | |
| 4,654,165 A | 3/1987 | Eisenberg | |
| 4,669,479 A | 6/1987 | Dunseath | |
| 4,725,997 A | 2/1988 | Urquhart et al. | |
| 4,763,659 A | 8/1988 | Dunseath | |
| 4,784,162 A | 11/1988 | Ricks | |
| 4,793,825 A | 12/1988 | Benjamin et al. | |
| 4,844,076 A | 7/1989 | Lesho | |
| 4,896,261 A | 1/1990 | Nolan | |
| 4,975,230 A | 12/1990 | Pinkhasov | |
| 4,987,897 A | 1/1991 | Funke | |
| 5,016,634 A | 5/1991 | Vock et al. | |
| 5,079,006 A | 1/1992 | Urquhart | |
| 5,167,626 A | 12/1992 | Casper | |
| 5,176,626 A | 1/1993 | Soehendra | |
| 5,261,402 A | 11/1993 | DiSabito | |
| 5,263,481 A | 11/1993 | Axelgaard et al. | |
| 5,281,287 A | 1/1994 | Lloyd | |
| 5,283,136 A | 2/1994 | Peled et al. | |
| 5,318,557 A | 6/1994 | Gross | |
| 5,394,882 A | 3/1995 | Mawhinney | |
| 5,458,141 A | 10/1995 | Neil et al. | |
| 5,485,841 A | 1/1996 | Watkin et al. | |
| 5,567,210 A | 10/1996 | Bates et al. | |
| 5,596,302 A | 1/1997 | Mastrocola et al. | |
| 5,600,548 A * | 2/1997 | Nguyen et al. | 363/41 |
| 5,634,468 A | 6/1997 | Platt | |
| 5,645,063 A | 7/1997 | Straka et al. | |
| 5,740,811 A | 4/1998 | Hedberg | |
| 5,792,048 A | 8/1998 | Schaefer | |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,868,136 A | 2/1999 | Fox | |
| 5,925,030 A | 7/1999 | Gross et al. | |
| 5,957,854 A | 9/1999 | Besson | |
| 5,974,124 A | 10/1999 | Schlueter, Jr. et al. | |
| 5,999,846 A | 12/1999 | Pardey et al. | |
| 6,038,464 A | 3/2000 | Axelgaard et al. | |
| 6,042,710 A | 3/2000 | Dubrow | |
| 6,047,203 A | 4/2000 | Sackner | |
| 6,081,734 A | 6/2000 | Batz | |
| 6,095,985 A | 8/2000 | Raymond et al. | |
| 6,122,351 A | 9/2000 | Schlueter, Jr. et al. | |
| 6,141,592 A | 10/2000 | Pauly | |
| 6,200,265 B1 | 3/2001 | Walsh et al. | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 * | 6/2001 | Sieben et al. | 604/891.1 |
| 6,269,058 B1 * | 7/2001 | Yamanoi et al. | 369/47.28 |
| 6,285,897 B1 | 9/2001 | Kilcoyne et al. | |
| 6,287,252 B1 | 9/2001 | Lugo | |
| 6,288,629 B1 * | 9/2001 | Cofino et al. | 340/10.1 |
| 6,289,238 B1 | 9/2001 | Besson | |
| 6,315,719 B1 | 11/2001 | Rode et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,477,424 B1 | 11/2002 | Thompson et al. | |
| 6,496,705 B1 | 12/2002 | Ng et al. | |
| 6,526,315 B1 | 2/2003 | Inagawa | |
| 6,544,174 B2 | 4/2003 | West | |
| 6,564,079 B1 | 5/2003 | Cory | |
| 6,577,893 B1 | 6/2003 | Besson | |
| 6,579,231 B1 | 6/2003 | Phipps | |
| 6,609,018 B2 | 8/2003 | Cory | |
| 6,612,984 B1 | 9/2003 | Kerr | |
| 6,632,175 B1 | 10/2003 | Marshall | |
| 6,632,216 B2 | 10/2003 | Houzego et al. | |
| 6,643,541 B2 | 11/2003 | Mok et al. | |
| 6,654,638 B1 | 11/2003 | Sweeney | |
| 6,663,846 B1 | 12/2003 | McCombs | |
| 6,673,474 B2 | 1/2004 | Yamamoto | |
| 6,680,923 B1 | 1/2004 | Leon | |
| 6,689,117 B2 | 2/2004 | Sweeney et al. | |
| 6,694,161 B2 | 2/2004 | Mehrotra | |
| 6,704,602 B2 | 3/2004 | Berg et al. | |
| 6,720,923 B1 | 4/2004 | Hayward et al. | |
| 6,738,671 B2 | 5/2004 | Christophersom et al. | |
| 6,740,033 B1 | 5/2004 | Olejniczak et al. | |
| 6,745,082 B2 | 6/2004 | Axelgaard et al. | |
| 6,755,783 B2 | 6/2004 | Cosentino | |
| 6,757,523 B2 | 6/2004 | Fry | |
| 6,800,060 B2 | 10/2004 | Marshall | |
| 6,801,137 B2 | 10/2004 | Eggers et al. | |
| 6,822,554 B2 | 11/2004 | Vrijens et al. | |
| 6,836,862 B1 | 12/2004 | Erekson et al. | |
| 6,839,659 B2 | 1/2005 | Tarassenko et al. | |
| 6,840,904 B2 | 1/2005 | Goldberg | |
| 6,842,636 B2 | 1/2005 | Perrault | |
| 6,845,272 B1 | 1/2005 | Thomsen | |
| 6,864,780 B2 | 3/2005 | Doi | |
| 6,879,810 B2 | 4/2005 | Bouet | |
| 6,909,878 B2 | 6/2005 | Haller | |
| 6,922,592 B2 | 7/2005 | Thompson et al. | |
| 6,928,370 B2 | 8/2005 | Anuzis et al. | |
| 6,929,636 B1 | 8/2005 | von Alten | |
| 6,937,150 B2 | 8/2005 | Medema | |
| 6,942,616 B2 | 9/2005 | Kerr | |
| 6,951,536 B2 | 10/2005 | Yokoi | |
| 6,957,107 B2 | 10/2005 | Rogers et al. | |
| 6,968,153 B1 | 11/2005 | Heinonen | |
| 6,987,965 B2 | 1/2006 | Ng et al. | |
| 6,990,082 B1 | 1/2006 | Zehavi et al. | |
| 7,002,476 B2 | 2/2006 | Rapchak | |
| 7,004,395 B2 | 2/2006 | Koenck | |
| 7,009,634 B2 | 3/2006 | Iddan et al. | |
| 7,009,946 B1 | 3/2006 | Kardach | |
| 7,013,162 B2 | 3/2006 | Gorsuch | |
| 7,016,648 B2 | 3/2006 | Haller | |
| 7,020,508 B2 | 3/2006 | Stivoric | |
| 7,024,248 B2 | 4/2006 | Penner | |
| 7,031,745 B2 | 4/2006 | Shen | |
| 7,031,857 B2 | 4/2006 | Tarassenko et al. | |
| 7,039,453 B2 | 5/2006 | Mullick | |
| 7,046,649 B2 | 5/2006 | Awater et al. | |
| 7,118,531 B2 | 10/2006 | Krill | |
| 7,127,300 B2 | 10/2006 | Mazar et al. | |
| 7,146,228 B2 | 12/2006 | Nielsen | |
| 7,146,449 B2 | 12/2006 | Do et al. | |
| 7,149,581 B2 | 12/2006 | Goedeke et al. | |
| 7,154,071 B2 | 12/2006 | Sattler et al. | |
| 7,155,232 B2 | 12/2006 | Godfrey et al. | |
| 7,160,258 B2 | 1/2007 | Imran | |
| 7,164,942 B2 | 1/2007 | Avrahami | |
| 7,171,166 B2 | 1/2007 | Ng et al. | |
| 7,171,177 B2 | 1/2007 | Park et al. | |
| 7,171,259 B2 | 1/2007 | Rytky | |
| 7,187,960 B2 | 3/2007 | Abreu | |
| 7,188,767 B2 | 3/2007 | Penuela | |
| 7,194,038 B1 | 3/2007 | Inkinen | |
| 7,206,630 B1 | 4/2007 | Tarler | |
| 7,209,790 B2 | 4/2007 | Thompson et al. | |
| 7,215,660 B2 | 5/2007 | Perlman | |
| 7,215,991 B2 | 5/2007 | Besson | |
| 7,218,967 B2 | 5/2007 | Bergelson | |
| 7,231,451 B2 | 6/2007 | Law | |
| 7,243,118 B2 | 7/2007 | Lou | |
| 7,246,521 B2 | 7/2007 | Kim | |

| Patent | Date | Name |
|---|---|---|
| 7,249,212 B2 | 7/2007 | Do |
| 7,252,792 B2 | 8/2007 | Perrault |
| 7,253,716 B2* | 8/2007 | Lovoi et al. ................... 340/10.1 |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2* | 6/2008 | Danowski et al. ......... 340/572.1 |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1* | 8/2008 | Kroll et al. ................. 340/573.1 |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2* | 6/2009 | Cole ........................ 340/573.1 |
| 7,575,005 B2 | 8/2009 | Mumford |
| 7,616,111 B2* | 11/2009 | Covannon et al. ....... 340/539.12 |
| 7,617,001 B2 | 11/2009 | Penner et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,809,399 B2 | 10/2010 | Lu |
| 7,844,341 B2 | 11/2010 | Von Arx et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukuda et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1* | 2/2005 | Ward, Jr. ....................... 340/505 |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |

| | | |
|---|---|---|
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1* | 12/2005 | Sengupta et al. .......... 340/573.1 |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1* | 12/2006 | Posamentier ................ 340/10.4 |
| 2006/0280227 A1 | 12/2006 | Pinkney |
| 2006/0282001 A1 | 12/2006 | Noel |
| 2006/0289640 A1* | 12/2006 | Mercure et al. .............. 235/435 |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123659 A1 | 5/2007 | Wu et al. |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowski |
| 2008/0020037 A1 | 1/2008 | Robertson |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0046038 A1 | 2/2008 | Hill |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1* | 11/2008 | Kroll et al. ...................... 607/60 |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |

| | | | | | | |
|---|---|---|---|---|---|---|
| 2009/0082645 A1 | 3/2009 | Hafezi et al. | | 2009/0281539 A1 | 11/2009 | Selig |
| 2009/0088618 A1 | 4/2009 | Armeson | | 2009/0295548 A1 | 12/2009 | Ronkka |
| 2009/0099435 A1 | 4/2009 | Say et al. | | 2009/0296677 A1 | 12/2009 | Mahany |
| 2009/0110148 A1 | 4/2009 | Zhang | | 2009/0303920 A1 | 12/2009 | Mahany |
| 2009/0112626 A1 | 4/2009 | Talbot | | 2009/0312619 A1 | 12/2009 | Say et al. |
| 2009/0124871 A1 | 5/2009 | Arshak | | 2009/0318761 A1 | 12/2009 | Rabinovitz |
| 2009/0131774 A1 | 5/2009 | Sweitzer | | 2009/0318779 A1 | 12/2009 | Tran |
| 2009/0135886 A1 | 5/2009 | Robertson et al. | | 2009/0318783 A1 | 12/2009 | Rohde |
| 2009/0157113 A1 | 6/2009 | Marcotte | | 2009/0318793 A1 | 12/2009 | Datta |
| 2009/0157358 A1 | 6/2009 | Kim | | 2010/0010330 A1 | 1/2010 | Rankers |
| 2009/0161602 A1 | 6/2009 | Matsumoto | | 2010/0049006 A1 | 2/2010 | Magar |
| 2009/0163789 A1 | 6/2009 | Say et al. | | 2010/0049012 A1 | 2/2010 | Dijksman et al. |
| 2009/0171180 A1 | 7/2009 | Pering | | 2010/0049069 A1 | 2/2010 | Tarassenko et al. |
| 2009/0173628 A1 | 7/2009 | Say et al. | | 2010/0056878 A1 | 3/2010 | Partin |
| 2009/0177055 A1 | 7/2009 | Say et al. | | 2010/0056891 A1 | 3/2010 | Say et al. |
| 2009/0177056 A1 | 7/2009 | Say et al. | | 2010/0056939 A1 | 3/2010 | Tarassenko et al. |
| 2009/0177057 A1 | 7/2009 | Say et al. | | 2010/0057041 A1 | 3/2010 | Hayter |
| 2009/0177058 A1 | 7/2009 | Say et al. | | 2010/0062709 A1 | 3/2010 | Kato |
| 2009/0177059 A1 | 7/2009 | Say et al. | | 2010/0063438 A1 | 3/2010 | Bengtsson |
| 2009/0177060 A1 | 7/2009 | Say et al. | | 2010/0063841 A1 | 3/2010 | D'Ambrosia et al. |
| 2009/0177061 A1 | 7/2009 | Say et al. | | 2010/0069002 A1 | 3/2010 | Rong |
| 2009/0177062 A1 | 7/2009 | Say et al. | | 2010/0099967 A1 | 4/2010 | Say et al. |
| 2009/0177063 A1 | 7/2009 | Say et al. | | 2010/0099968 A1 | 4/2010 | Say et al. |
| 2009/0177064 A1 | 7/2009 | Say et al. | | 2010/0099969 A1 | 4/2010 | Say et al. |
| 2009/0177065 A1 | 7/2009 | Say et al. | | 2010/0100077 A1 | 4/2010 | Rush |
| 2009/0177066 A1 | 7/2009 | Say et al. | | 2010/0100078 A1 | 4/2010 | Say et al. |
| 2009/0182206 A1 | 7/2009 | Najafi | | 2010/0106001 A1 | 4/2010 | Say et al. |
| 2009/0182212 A1 | 7/2009 | Say et al. | | 2010/0118853 A1 | 5/2010 | Godfrey |
| 2009/0182213 A1 | 7/2009 | Say et al. | | 2010/0139672 A1 | 6/2010 | Kroll et al. |
| 2009/0182214 A1 | 7/2009 | Say et al. | | 2010/0168659 A1 | 7/2010 | Say et al. |
| 2009/0182215 A1 | 7/2009 | Say et al. | | 2010/0179398 A1 | 7/2010 | Say et al. |
| 2009/0182388 A1 | 7/2009 | Von Arx | | 2010/0185055 A1 | 7/2010 | Robertson |
| 2009/0187088 A1 | 7/2009 | Say et al. | | 2010/0191073 A1 | 7/2010 | Tarassenko et al. |
| 2009/0187089 A1 | 7/2009 | Say et al. | | 2010/0210299 A1 | 8/2010 | Gorbachov |
| 2009/0187090 A1 | 7/2009 | Say et al. | | 2010/0222652 A1 | 9/2010 | Cho |
| 2009/0187091 A1 | 7/2009 | Say et al. | | 2010/0228113 A1 | 9/2010 | Solosko |
| 2009/0187092 A1 | 7/2009 | Say et al. | | 2010/0234706 A1 | 9/2010 | Gilland |
| 2009/0187093 A1 | 7/2009 | Say et al. | | 2010/0234715 A1 | 9/2010 | Shin |
| 2009/0187094 A1 | 7/2009 | Say et al. | | 2010/0234914 A1 | 9/2010 | Shen |
| 2009/0187095 A1 | 7/2009 | Say et al. | | 2010/0245091 A1 | 9/2010 | Singh |
| 2009/0187381 A1 | 7/2009 | King et al. | | 2010/0249881 A1 | 9/2010 | Corndorf |
| 2009/0192351 A1 | 7/2009 | Nishino | | 2010/0256461 A1 | 10/2010 | Mohamedali |
| 2009/0192368 A1 | 7/2009 | Say et al. | | 2010/0259543 A1 | 10/2010 | Tarassenko et al. |
| 2009/0192369 A1 | 7/2009 | Say et al. | | 2010/0268048 A1 | 10/2010 | Say et al. |
| 2009/0192370 A1 | 7/2009 | Say et al. | | 2010/0268049 A1 | 10/2010 | Say et al. |
| 2009/0192371 A1 | 7/2009 | Say et al. | | 2010/0268050 A1 | 10/2010 | Say et al. |
| 2009/0192372 A1 | 7/2009 | Say et al. | | 2010/0274111 A1 | 10/2010 | Say et al. |
| 2009/0192373 A1 | 7/2009 | Say et al. | | 2010/0280345 A1 | 11/2010 | Say et al. |
| 2009/0192374 A1 | 7/2009 | Say et al. | | 2010/0280346 A1 | 11/2010 | Say et al. |
| 2009/0192375 A1 | 7/2009 | Say et al. | | 2010/0298730 A1 | 11/2010 | Tarassenko et al. |
| 2009/0192376 A1 | 7/2009 | Say et al. | | 2010/0312580 A1 | 12/2010 | Tarassenko et al. |
| 2009/0192377 A1 | 7/2009 | Say et al. | | | | |
| 2009/0192378 A1 | 7/2009 | Say et al. | | | | |
| 2009/0192379 A1 | 7/2009 | Say et al. | | | | |
| 2009/0198115 A1 | 8/2009 | Say et al. | | | | |
| 2009/0198116 A1 | 8/2009 | Say et al. | | | | |
| 2009/0198175 A1 | 8/2009 | Say et al. | | | | |
| 2009/0203964 A1 | 8/2009 | Shimizu et al. | | | | |
| 2009/0203971 A1 | 8/2009 | Sciarappa | | | | |
| 2009/0203972 A1 | 8/2009 | Heneghan | | | | |
| 2009/0203978 A1 | 8/2009 | Say et al. | | | | |
| 2009/0204265 A1 | 8/2009 | Hackett | | | | |
| 2009/0210164 A1 | 8/2009 | Say et al. | | | | |
| 2009/0216101 A1 | 8/2009 | Say et al. | | | | |
| 2009/0216102 A1 | 8/2009 | Say et al. | | | | |
| 2009/0227204 A1 | 9/2009 | Robertson et al. | | | | |
| 2009/0227876 A1 | 9/2009 | Tran | | | | |
| 2009/0227940 A1 | 9/2009 | Say et al. | | | | |
| 2009/0227941 A1 | 9/2009 | Say et al. | | | | |
| 2009/0228214 A1 | 9/2009 | Say et al. | | | | |
| 2009/0231125 A1 | 9/2009 | Baldus | | | | |
| 2009/0234200 A1 | 9/2009 | Husheer | | | | |
| 2009/0243833 A1 | 10/2009 | Huang | | | | |
| 2009/0253960 A1 | 10/2009 | Takenaka et al. | | | | |
| 2009/0256702 A1 | 10/2009 | Robertson | | | | |
| 2009/0264714 A1 | 10/2009 | Chou | | | | |
| 2009/0264964 A1 | 10/2009 | Abrahamson | | | | |
| 2009/0265186 A1 | 10/2009 | Tarassenko et al. | | | | |
| 2009/0273467 A1 | 11/2009 | Elixmann | | | | |

FOREIGN PATENT DOCUMENTS

| | | |
|---|---|---|
| EP | 1789128 | 5/2007 |
| EP | 2143369 | 1/2010 |
| JP | 61072712 | 4/1986 |
| JP | 2005-304880 | 4/2005 |
| WO | 8802237 | 4/1988 |
| WO | WO8802237 | 4/1988 |
| WO | WO9308734 | 5/1993 |
| WO | WO9319667 | 10/1993 |
| WO | WO9843537 | 10/1998 |
| WO | WO9959465 | 11/1999 |
| WO | WO0033246 | 6/2000 |
| WO | WO0100085 | 1/2001 |
| WO | 2001/47466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004066834 | 8/2004 |
| WO | WO2004068881 | 8/2004 |
| WO | WO2004109316 | 12/2004 |
| WO | WO2005011237 | 2/2005 |

| | | |
|---|---|---|
| WO | 2005/020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | 2006/116718 | 2/2006 |
| WO | WO2006027586 | 3/2006 |
| WO | 2006/055892 | 5/2006 |
| WO | 2006/055956 | 5/2006 |
| WO | WO2006075016 | 7/2006 |
| WO | WO2006100620 | 9/2006 |
| WO | 2006/104843 | 10/2006 |
| WO | 2006/116718 | 11/2006 |
| WO | 2006/127355 | 11/2006 |
| WO | WO 2006116718 A2 * | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | WO2007014527 | 2/2007 |
| WO | 2007/027660 | 3/2007 |
| WO | 2007/028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | 2007130491 | 11/2007 |
| WO | WO2007127316 | 11/2007 |
| WO | WO2007127879 | 11/2007 |
| WO | WO2007128165 | 11/2007 |
| WO | 2007/149546 | 12/2007 |
| WO | 2007/149546 A2 | 12/2007 |
| WO | WO2007143535 | 12/2007 |
| WO | 2008/008281 | 1/2008 |
| WO | WO2008030482 | 3/2008 |
| WO | 2008/052136 | 5/2008 |
| WO | 2008/052136 A2 | 5/2008 |
| WO | 2008/063626 | 5/2008 |
| WO | 2008/063626 A2 | 5/2008 |
| WO | 2008/066617 | 6/2008 |
| WO | WO2008076464 | 6/2008 |
| WO | WO2008089232 | 7/2008 |
| WO | WO2008091683 | 7/2008 |
| WO | 2008/095183 | 8/2008 |
| WO | 2008/095183 A2 | 8/2008 |
| WO | 2008/101107 | 8/2008 |
| WO | WO2008097652 | 8/2008 |
| WO | 2008/112577 | 9/2008 |
| WO | 2008/112577 A1 | 9/2008 |
| WO | 2008/112578 | 9/2008 |
| WO | 2008/112578 A1 | 9/2008 |
| WO | 20080120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | 2010019778 | 2/2010 |
| WO | 2010057049 | 5/2010 |
| WO | WO2010107563 | 9/2010 |
| WO | WO2010135516 | 11/2010 |

OTHER PUBLICATIONS

Mackay et al,. Endoradiosonde. Nature 1957;179(4572):1239-40, 179.

Zworkin, A 'radio pill.' Nature 1957;179:898.

Yao et al., Low Power Digital Communication in Implantable Devices Using Volume Conduction of Biological Tissues. Proceedings of the 28th IEEE, EMBC Annual International Conference (Aug. 30-Sep. 3, 2006); New York, USA.

McKenzie et al., Validation of a new telemetric core temperature monitor. J. Therm. Biol. 2004;29(7-8):605-11.

Tatbul et al, Confidence-based data management for personal area sensor networks. ACM International Conference Proceeding Series 2004;72.

Zimmerman, Personal Area Networks: Near-field intrabody communication. IBM Systems Journal 1996;35 (3-4):609-17.

Mini Mitter Co, Inc. 510(k) Premarket Notification Mini-Logger for Diagnostic Spirometer. Sep. 21, 1999.

Philips Respironics. 510(k) Premarket Notification for VitalSense. Apr. 22, 2004.

Mini Mitter Co, Inc. Actiheart. Traditional 510(k) Summary. Sep. 27, 2005.

Mini Mitter Co, Inc. VitalSense Integrated Physiological Monitoring System. Product Description.

Mini Mitter Co, Inc. VitalSense—Wireless Vital Signs Monitoring. Temperatures.com Mar. 31, 2009.

Mini Mitter Co, Inc. Noninvasive technology to help your studies succeed. Mini Mitter.com Mar. 31, 2009.

Barrie, Heidelberg pH capsule gastric analysis. Textbook of Natural Medicine, 1992, Pizzorno, Murray & Barrie.

Carlson et al., Evaluation of a non-invasive respiratory monitoring system for sleeping subjects. Physiological Measurement 1999;20(1):53.

Mojaverian et al., Estimation of gastric residence time of the Heidelberg capsule in humans: effect of varying food composition. Gastroenterology 1985;89(2):392-7.

Xiaoming et al., A telemedicine system for wireless home healthcare based on bluetooth and the internet. Telemedicine Journal and e-health 2004;10(S2):S110-6.

Intromedic, MiroCam Innovative Capsule Endoscope Pamphlet. 8 pages (http://www.intromedic.com/en/product/productInfo.asp).

Mini Mitter Co, Inc. 510(k) Premarket Notification for VitalSense. Apr. 22, 2004.

Heydari et al., "Analysis of the PLL jitter due to power/ground and substrate noise"; IEEE Transactions on Circuits and Systems (2004) 51(12): 2404-16.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Yang et al., "Fast-switching frequency synthesizer with a discriminator-aided phase detector" IEEE Journal of Solid-State Circuits (2000) 35(10): 1445-52.

"Smartlife awarded patent for knitted transducer" Innovation in Textiles News: http://www.innovationintextiles.com/articles/208.php; 2pp. (2009).

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. Of Eng. & Electron., Edinburgh Univ., UK; (2003); abstract.

Brock, "Smart Medicine: The Application of Auto-ID Technology to Healthcare" Auto-ID Labs (2002) http://www.autoidlabs.org/uploads/media/MIT-AUTOID-WH-010.pdf.

Delvaux et al., "Capsule endoscopy: Technique and indications" Clinical Gastoenterology (2008) vol. 22, Issue 5, pp. 813-837.

Fawaz et al., "Enhanced Telemetry System using CP-QPSK Band—Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.)4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Melanson, "Walkers swallow RFID pills for science" Engadget (2008); http://www.engadget.com/2008/07/29/walkers-swallow-rfid-pills-for-science/.

"New 'smart pill' to track adherence" E-Health-Insider (2010) http://www.e-health-insider.com/news/5910/new_'smart_pill'_monitors_medicines.

"RFID "pill" monitors marchers" RFID News (2008) http://www.rfidnews.org/2008/07/23/rfid-pill-monitors-marchers/.

"SensiVida minimally invasive clinical systems" Investor Presentation Oct. 2009 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" SmartPill, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1.

University of Florida News "Rx for health: Engineers design pill that signals it has been swallowed" (2010) 2pp.; http://news.ufl.edu/2010/03/31/antenna-pill-2/.

Gilson, D.R. "Molecular dynamics simulation of dipole interactions", Department of Physics, Hull University, Dec. 2002, p. 1-43.

Li, P-Y, et al. "An electrochemical intraocular drug delivery device", Sensors and Actuators A 143 (2008) p. 41-48.

NPL_AntennaBasics.pdf, p. 1-3.

Santini, J.T. et al, "Microchips as controlled drug delivery-devices", Agnew. Chem. Int. Ed. 2000, vol. 39, p. 2396-2407.

Shawgo, R.S. et al. "BioMEMS from drug delivery", Current Opinion in Solid State and Material Science 6 (2002), p. 329-334.

Soper, S.A. et al. "Bio-Mems Technologies and Applications", Chapter 12, "MEMS for Drug Delivery", p. 325-346.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

Descpription of ePatch Technology Platform for ECG and EMG, located it http://www.madebydelta.com/imported/imagesiDELTA_Web/documents/ME/ePatch_ECG_EMG.pdf. Dated Sep. 2, 2010.

Coury, L. "Conductance Measurement Part 1: Theory"; Current Separations, 18:3 (1999) p. 91-96.

ISFET—Ion Sensitive Field-Effect Transistor; Microsens S.A. pdf document. pp. 1-4.

Walkey, "MOSFET Struture and Processing"; 97.398* Physical Electronics Lecture 20; pp. 1-24.

Watson, et al., "Determination of the relationship between the pH and conductivity of gastric juice" Physiol Meas. 17 (1996) pp. 21-27.

* cited by examiner

RFID ANTENNA FOR IN-BODY DEVICE

CROSS-REFERENCE TO RELATED APPLICATIONS

Pursuant to 35 U.S.C. §119(e), this application claims priority to the filing date of U.S. Provisional Patent Application Ser. No. 60/940,063 filed on May 24, 2007, the disclosure of which application is herein incorporated by reference.

INTRODUCTION

As medical technology advances, many diagnostic and therapeutic activities are carried out with increasingly small implantable medical or ingestible medical devices. Implantable and ingestible medical devices can be configured to perform a variety of different functions, including but not limited to: diagnostic functions, e.g., where the devices include one or more sensors; therapeutic functions, e.g., where the devices enable therapeutic action, such as delivery of an electrical pulse, delivery of a pharmaceutically active agent; etc.

With implantable and ingestible medical and related technologies, there is always a desire to make the devices smaller, e.g., to provide for increased ease of use, etc. To decrease size, individual components of the devices must be designed with a reduced overall physical size, and yet maintain functionality.

One type of component that is present in many implantable and ingestible devices is an antenna, e.g., in the form of a signal transmitter. There is continued interest in the development of signal transmission antennas for in-body devices that have adequate and reliable functionality and are physiologically compatible such that they can be employed with in-body devices, such as implantable and ingestible devices.

SUMMARY

RFID antennas for ingestible devices, such as ingestible event markers, are provided. Aspects of the ingestible devices of the invention include RFID signal transmission antennas with a battery that is activated upon being exposed to fluid in the body. Embodiments of the RFID antennas are configured to emit a detectable signal upon contact with a target physiological site. Embodiments of the invention are characterized by having an RFID tag that is readable only upon activation of a battery by contact with a target physiological site, e.g., the stomach. Also provided are methods of making and using the devices of the invention.

Aspects of the invention include the ability of the RFID antenna to receive an input signal from a reader or from a connected battery. Embodiments include RFID antennas with a power source, e.g. a battery, which is only activated on contact with fluid in the body. In some embodiments, the RFID antenna can conform to the dimensions of the pill prior to ingestion. In some embodiments, the antenna structure can be folded, rolled, coiled, or otherwise adjusted to fit on or inside a carrier structure. Upon ingestion of the carrier structure, the carrier structure can degrade in some manner, e.g., by being dissolved or physically eroded. In some embodiments, the RFID antenna is then activated, such as by contact with fluid in the body.

In some embodiments, the antenna and associated chip are printed on a biocompatible substrate. The antenna can be integrated into the carrier composition itself through a manufacturing process. This can involve use of a mold, or other methods. The antenna and associated chip can be added in a post-processing step, through circuit printing or mechanical techniques, among others.

The RFID antenna of the invention can be utilized in many configurations and transmission methods. Examples include low frequency RFID using magnetic coupling, and high frequency RFID using electromagnetic radiative coupling.

Upon activation, a signal broadcasted from the identifier may be received by another device, e.g., a receiver, either inside or near the body, as described in greater detail below.

Embodiments of the invention include ingestible event marker compositions having an identifier and a pharmaceutically acceptable carrier. The identifier is characterized by being activated upon contact with a target site fluid present at a target site. Aspects of the identifier include the presence of an RFID signal transmission antenna. Upon activation, a signal broadcasted from the identifier may be received by another device, e.g., a receiver, either inside or near the body, which may then record that the pharmaceutical composition has in fact reached the target site.

DETAILED DESCRIPTION

Figure 1:
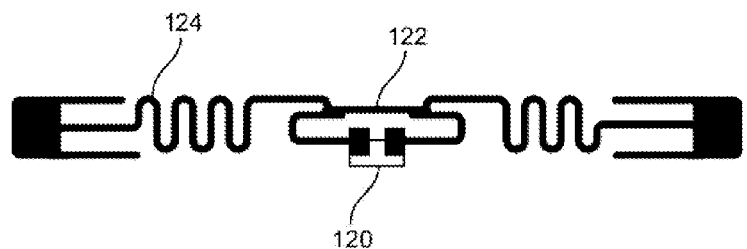
FIG. 1 shows a prior art RFID tag.

RFID antennas for ingestible devices, such as ingestible event markers, are provided. Aspects of the ingestible devices of the invention include RFID signal transmission antennas with a battery that is activated upon being exposed to fluid in the body. Embodiments of the in-body devices are configured to emit a detectable signal upon contact with a target physiological site, such as with a battery completion format. Also provided are methods of making and using the devices of the invention.

In further describing the invention in greater detail, embodiments of the RFID antennas and in-body devices that include the same are reviewed first, followed by a discussion of systems having devices that include the in-body devices, and methods of using such devices and systems. Also reviewed in greater detail below are kits that include the in-body devices of the invention.

In-Body Devices Having RFID Antennas

As summarized above, the invention provides in-body devices having RFID signal transmission antennas. An in-body device is a device that is configured to be used inside of a living body. Examples of in-body devices include, but are not limited to: implantable devices, e.g., implantable therapeutic devices, such as but not limited to stents, drug delivery devices, orthopedic implants, etc.: implantable diagnostic devices, e.g., sensors, biomarker recorders, etc.; and ingestible devices, e.g., ingestible event markers, as described in greater detail below, etc.

One type of in-body device in which the RFID antenna of the invention finds use is an ingestible event marker. For ease of description, the in-body devices of the invention will now be further described in terms of embodiments where the antenna is part of an identifier of an ingestible event marker. However, as indicated above, the antennas of the invention find use in devices other than ingestible event markers, and therefore antennas of the invention are not limited to those configured for use in ingestible event markers (IEM).

The identifier of the IEM compositions is one that generates (i.e., emits) a detectable signal upon contact of the identifier with a target physiological site. The identifiers of the present compositions may vary depending on the particular embodiment and intended application of the composition so long as they are activated (i.e., turned on) upon contact with a target physiological location, e.g., stomach. As such, an ingestible event marker may comprise an identifier that emits a signal when activated at a target site, e.g. when it contacts a target body (i.e., physiological) site. The identifier may be any component or device that is capable of providing a detectable signal following activation, e.g., upon contact with the target site. The identifier therefore comprises a signal generation element, e.g. a RFID antenna. In certain embodiments, the identifier emits a signal once the composition comes into contact with a physiological target site, e.g., the stomach. Depending on the embodiment, the target physiological site or location may vary, where representative target physiological sites of interest include, but are not limited to: a location in the gastrointestinal tract, such as the mouth, esophagus, stomach, small intestine, large intestine, etc. In certain embodiments, the identifier is configured to be activated upon contact with fluid at the target site, e.g. stomach fluid, regardless of the particular composition of the target site. In some embodiments, the identifier is configured to be activated by interrogation, following contact of the composition with a target physiological site. In some embodiments, the identifier is configured to be activated at a target site, wherein the target site is reached after a specified period of time.

Depending on the needs of a particular application, the signal obtained from the identifier may be a generic signal, e.g., a signal that merely identifies that the composition has contacted the target site, or a unique signal, e.g., a signal which in some way uniquely identifies that a particular ingestible event marker from a group or plurality of different markers in a batch has contacted a target physiological site. As such, the identifier may be one that, when employed with a batch of unit dosages, e.g., a batch of tablets, emits a signal which cannot be distinguished from the signal emitted by the identifier of any other unit dosage member of the batch. In yet other embodiments, the identifier emits a signal that uniquely identifies that particular identifier. Accordingly, in certain embodiments the identifier emits a unique signal that distinguishes one class of identifier from other types of identifiers. In certain embodiments, the identifier emits a unique signal that distinguishes that identifier from other identifiers. In certain embodiments, the identifier emits a signal that is unique, i.e., distinguishable, from a signal emitted by any other identifier ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about a given event, or provide an identifying code, which may be used to retrieve information about the event from a database, i.e., a database linking identifying codes with compositions.

The identifier may generate a variety of different types of signals, including but not limited to: RF signals, magnetic signals, conductive (near field) signals, acoustic signals, etc. Of interest in certain embodiments are the specific signals described in pending PCT application serial no. PCT/US2006/16370 filed on Apr. 28, 2006; the disclosures of various types of signals in this application being specifically incorporated herein by reference. The transmission time of the identifier may vary, where in certain embodiments the transmission time may range from about 0.1 μsec to about 48 hours or longer, e.g., from about 0.1 μsec to about 24 hours or longer, such as from about 0.1 μsec to about 4 hours or longer, such as from about 1 sec to about 4 hours, including about 1 minute to about 10 minutes. Depending on the given embodiment, the identifier may transmit a signal once or transmit a signal two or more times, such that the signal may be viewed as a redundant signal.

The identifiers may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. In addition or alternatively, the identifier may be an identifier that emits a signal when interrogated after it has been activated. Identifier components of embodiments of the invention have: (a) an activation component; and (b) a signal generation component, where the signal generation component is activated by the activation component to produce an identifying signal, e.g., as described above.

The activation component is a component that activates the signal generation element of the identifier to provide a signal, e.g., by emission or upon interrogation, following contact of the composition with a target physiological site of interest, such as the stomach. As reviewed in co-pending PCT application serial no. PCT/US2006/016370, activation of the identifier may be achieved in a number of different ways, where such approaches include, but are not limited to: battery completion, battery connection, etc. The different activation approaches disclosed in this co-pending application may be readily adapted to provide activation, as described herein, and as such are herein incorporated by reference in their entirety.

Embodiments of activation elements based on battery completion formats according to the invention employ in-body battery power sources, where when activated, the in-body battery power source includes, a cathode, an anode, and an electrolyte. In such embodiments, when the cathode and anode come into contact with stomach fluid, the stomach fluid acts as the electrolyte component of the battery, such that the added component of the stomach fluid thus completes the battery.

In certain embodiments, the battery that is employed is one that comprises two dissimilar electrochemical materials which constitute the two electrodes (e.g., anode and cathode) of the battery. When the electrode materials come in contact with the body fluid, such as stomach acid or other types of fluid (either alone or in combination with a dried conductive medium precursor), a potential difference, i.e., a voltage, is generated between the electrodes as a result of the respective oxidation and reduction reactions occurring at the two electrodes (such that a voltaic cell or battery is produced). Accordingly, in embodiments of the invention, power sources are configured such that when the two dissimilar materials are exposed to the target site, e.g., the stomach, the digestive tract, etc., a voltage is generated. The two dissimilar materials in an electrolyte are at different potentials. In certain of these embodiments, the in-body battery power source may be viewed as a power source that exploits electrochemical reaction in an ionic solution such as gastric fluid, blood, or other bodily fluids and some tissues.

The dissimilar materials making up the electrodes can be made of any two materials appropriate to the environment in which the identifier will be operating. The active materials are any pair of materials with different electrochemical potentials. For instance, in some embodiments where the ionic solution comprises stomach acids, electrodes may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow the identifier to perform its intended function. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the battery electrodes. In certain embodiments, electrode materials are chosen to provide for a voltage upon contact with the target physiological site, e.g., the stomach, sufficient to drive the signal generation element of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Materials and pairings of interest include, but are not limited to those reported in Table 1 below.

TABLE 1

|  | Anode | Cathode |
|---|---|---|
| Metals | Magnesium, Zinc Sodium (†), Lithium (†) Iron and alloys thereof, e.g., Al and Zn alloys of Mg |  |
| Salts |  | Copper salts: iodide, chloride, bromide, sulfate, formate, (other anions possible) $Fe^{3+}$ salts: e.g. orthophosphate, pyrophosphate, (other anions possible) Oxygen or hydrogen (††) on platinum, gold or other catalytic surfaces |
| Intercalation compounds | Graphite with Li, K, Ca, Na, Mg | Vanadium oxide Manganese oxide |

(†) Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).
(††) Dissolved oxygen can also serve as a cathode. In this case, the dissolved oxygen in the bodily fluids would be reduced to OH– at a suitable catalytic surface such at Pt or gold. Also of interest dissolved hydrogen in a hydrogen reduction reaction.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride (CuCl) as the cathode and magnesium (Mg) metal or magnesium alloy as the anode. Embodiments of the present invention use electrode materials that are not harmful to the human body.

Depending on the particular embodiment, the cathode and anode may be present on the same support or different supports, e.g., where two or more different supports are bonded together to produce the battery structure, e.g., as is present in a "flip-chip" embodiment. Similarly, the number of cathodes and anodes in a given battery may vary greatly depending on the embodiment, e.g., where a given embodiment may include a single battery having one anode and cathode, a single battery having multiple anodes and/or cathodes, or two or more distinct batteries each made up of one or more cathodes and/or anodes. Battery configurations of interest include, but are not limited to, those disclosed in PCT application serial no. PCT/US2006/016370 filed on Apr. 28, 2006 and titled "Pharma-Informatics System"; PCT application serial no. PCT/US2007/022257 filed on Oct. 17, 2007 and titled "In-vivo Low Voltage Oscillator for Medical Devices"; PCT application serial no. PCT/US2007/82563 filed on Oct. 25, 2007 and titled "Controlled Activation Ingestible Identifier"; U.S. patent application Ser. No. 11/776,480 filed Jul. 11, 2007 entitled "Acoustic Pharma Informatics System"; PCT/US2008/52845 filed on Feb. 1, 2008 and titled "Ingestible Event Marker Systems"; PCT/US08/53999 filed Feb. 14, 2008 and titled "In-Body Power Source Having High Surface Area Electrode," the disclosures of which applications (and particularly battery configurations disclosed therein) are herein incorporated by reference.

In addition to the activation component, e.g., battery component, as described above, ingestible event markers of the invention include a solid support. The solid support may vary depending on the nature of the IEM. In certain embodiments, the solid support is small, e.g., where it is dimensioned to have a width ranging from about 0.01 mm to about 100 mm, e.g., from about 0.1 mm to about 20 mm, including from about 0.5 mm to about 2 mm; a length ranging from about 0.01 mm to about 100 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm. The solid support element may take a variety of different configurations, such as but not limited to: a chip configuration, a cylinder configuration, a spherical configuration, a disc configuration, etc., where a particular configuration may be selected based on intended application, method of manufacture, etc. While the material from which the solid support is fabricated may vary considerably depending on the particular device for which the antenna is configured for use, in certain embodiments the solid support is made up of a semiconductor material, e.g., silicon.

In certain embodiments, the solid support is a semiconductor support that includes one or more circuit elements, where in certain embodiments the support is an integrated circuit. When present, integrated circuits include a number of distinct functional blocks, i.e., modules. Within a given solid support, at least some of, e.g., two or more, up to and including all of, the functional blocks, e.g., power source, processor, transmitter, etc., may be present in a single integrated circuit. By single integrated circuit is meant a single circuit structure that includes all of the different desired functional blocks for the device. In these embodiments, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

In addition to the activation component of the identifier, described above, identifiers of the invention also include a signal generation component. The signal generation component of the identifier element is a structure that, upon activation by the activation component, emits a detectable signal, e.g., that can be received by a receiver, e.g., as described in greater detail below. The signal generation component of certain embodiments can be any convenient device that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry, as developed in more detail below, which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

As summarized above, the signal generation component of the identifier includes a RFID antenna, which may serve as a distinct transmitter component that serves to transmit the generated signal to a remote receiver, which may be internal or external to the patient, as reviewed in greater detail below. The RFID antenna may also function as a signal receiver, and in certain embodiments may have both transmitter and receiver functionality, such that it is a transceiver. The antenna component may take a number of different configurations, e.g., depending on the type of signal that is generated and is to be emitted. In certain embodiments, the antenna component is made up of one or more electrodes. In certain embodiments, the antenna component is made up of one or more wires. In certain embodiments, the antenna component is made up of one or more coils. As such, the antenna may include a variety of different transmitters and/or receiver elements, e.g., electrodes, wires, coils, etc.

As reviewed above, the antennas of the invention are RFID antennas. In some embodiments, the RFID antenna or the antenna structure is flexible, such that it changes shape when the carrier component or carrier composition is dissolved or degraded after ingestion. The RFID antenna can therefore have a first configuration (e.g., a curved configuration) which conforms to pill dimensions prior to ingestion and a second configuration after ingestion, such that the RFID antenna has a greater effective area for signal transmission and/or reception in the second configuration.

In some embodiments, the RFID antenna or the antenna structure is degradable, such that it at least partially physically erodes, degrades, or dissolves after ingestion, such that the antenna and other component parts can easily pass through the body. This ability to be degraded or dissolved allows the antenna to conform to ingestible pill dimensions, but degrade after use, e.g. once signal generation or reception has taken place.

By "effective area" is meant the area of the antenna that can be used for signal generation and transmission. As the antenna gets smaller, the maximum distance at which the identifier with an RFID antenna is readable decreases. Therefore, as coil goes from a position or configuration that is rolled up or folded, for example, to a configuration that is open, i.e., with a maximal or at least an increased cross-sectional area, the ability of the antenna to both transmit and receive signals will be increased.

An RFID antenna of the prior art is shown in FIG. 1 with chip 120, loop 122, and antenna 124. In some embodiments, a similar antenna can be adapted for use in conjunction with the pharma-informatics system. RFID chip 120 has several distinct components, which can be summarized in three sections. There is logic, permanent flash memory, and analog circuitry which essentially performs digital to analog conversion and analog to digital conversion. There is a universal standard for commercial RFID, so that tags and readers from different manufacturers are compatible. Loop 122 is vital to the operability of the RFID tag. If it is desired for the RFID tag to be disabled so it is no longer readable, loop 122 can be broken.

In a typical commercial RFID application, an input signal is sent from the reader and picked up by the tag. This signal is sent at a predetermined frequency, such as 915 MHz. That frequency is received by the tag and used as a syncing frequency in the chip. There is encryption present on the chip, such that the bits encoded in the input signal must be in a specific pattern in order to pass the encryption lock. When the encryption is passed, the chip sends out a reflected signal with additional bits that are stored in the memory. The bit sequence sent by the tag is then recorded by the reader and used to identify the item that the tag is associated with. The backscatter is typically a much weaker signal than the input signal, but the whole system operates on low power. The current commercial standard calls for a reader with a power consumption of less than 1 $W/m^2$.

Anti-collision protocols are also typically built in to current RFID systems. Anti-collision allows for multiple tags to be read sequentially and then turned off so that the other tags can be read.

The flash memory in the tag also can be written to using an RF signal. A different set of encryption is used when writing to the memory than when reading from the memory.

Many aspects of currently available RFID systems can be changed to adapt them to be used in a pharma-informatics system. For example, the sync signal need not come from the reader. The signal can be created from a separate input clock from a connected battery. Alternatively, the syncing signal can be kept, but the RFID tag can be configured such that the backscatter is only enabled when the battery is active. When used in conjunction with a battery which is only activated upon being exposed to fluid in the body, the pills will not be readable while outside the body. When the pill is ingested, the battery turns on, and the RFID tag associated with the pill becomes readable. The presence of an RFID signal is an indication to the reader that the pill has been ingested and the active agent has been delivered.

There are many methods to configure the tag such that it is only readable after the battery is ingested. There can be a normally off transistor inserted in the tag such that it isolates a portion of the tag which is essential for its function. For example, if the logic is separated by a transistor which only turns on and closes the circuit once the battery is activated, the tag will not be readable until the battery turns on upon exposure to fluid in the body.

Figure 2:
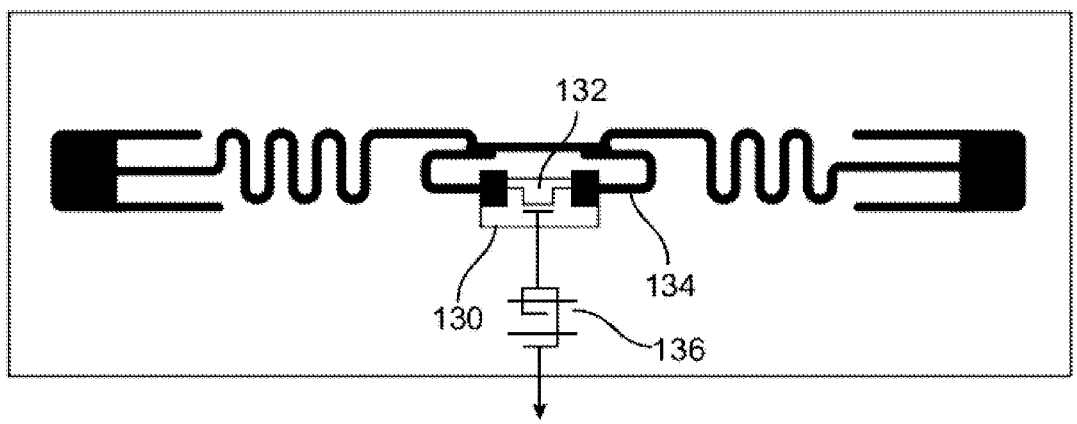
FIG. 2 shows an embodiment of an RFID tag which is only functional when an attached battery is activated.

FIG. 2 shows an example of a RFID tag according to an embodiment of the invention which will only be activated once a battery turns on. Chip 130 contains transistor 132 which is normally open, leaving the chip off and loop 134 open. Battery 136 powers up when exposed to fluid in the body, providing a voltage to transistor 132, which closes the circuit in chip 130 and allows the tag to be read by the reader. The input signal can be provided by the reader or powered by battery 136.

A Galvanic cell can also be used as a switch to activate the RFID tag. A galvanic cell comprising one material that can reduce to a metal, such as CuCl or CuI and another material that can be oxidized such as Mg, Zn, or Al can be placed in the tag to create an open circuit. It can be placed in a location where an open circuit will keep the tag from being read. When the galvanic cell comes in contact with fluid in the body after an encapsulation layer dissolves, it will reduce to a metal and complete the circuit, enabling the RFID tag to be read.

The RFID tag can also be configured such that it becomes no longer readable after a certain period of time. This is often desirable in pharmaceutical applications, because of privacy concerns. In embodiments where the RFID tag only becomes readable when a battery is activated, that battery can have a limited lifespan. Once the battery runs down, the RFID tag will become unreadable again.

Alternatively, the antenna can be manufactured on a material, such as a hydrogel, which swells when it comes in contact with the body. Once the pill dissolves in the body, the antenna substrate swells and breaks the antenna, rendering it no longer readable.

The RFID tag can be designed to operate over a wide range of frequencies. In some embodiments, frequency hopping can be built in to find the frequencies that are best suited for signal transmission in the body. This also can aid in anti-collision. The tag or the reader can tune the frequency of the RFID signal to minimize signal attenuation.

The RFID tag can be made small enough to be placed in or on a pill. In some embodiments, the RFID tag can be rolled or otherwise conformed to fit in a pill and deploy to a larger cross-sectional area once the pill dissolves in the body. In some embodiments of the RFID pill antenna, the antenna can be integrated into the pill during manufacturing, rather than added later. In some embodiments of the RFID pill antenna, the antenna can be printed directly on the outside of the pill. This allows the addition of the antenna, and optionally the chip, to be a post-processing step. This is highly advantageous because a signal transmission system including a transmitter chip and antenna can be added to any pre-manufactured pill in a post-processing step. Embodiments as described above are disclosed in International Patent Application Serial No. US08/56299, and incorporated herein by reference. As the antenna gets smaller, the maximum distance at which the RFID tag is readable goes down. The power of the reader can be increased to compensate for this and increase the readable distance. Also, utilizing a battery onboard the tag can increase the readable distance. The RFID tag can be as small as about 5 mm to about 10 cm, more specifically about 5 mm to about 5 cm, most specifically about 1 cm to about 2 cm. The larger tags can be conformed to fit inside the pill and deploy once the pill has dissolved in the body.

In other embodiments, the RFID antenna can be built with multiple metal layers that create a larger effective cross section. The antenna can also utilize a material with a high dielectric, such as fluorinated dielectric materials, that essentially act to compress the electromagnetic wave and help to pick it up with a smaller antenna area.

Other means for securing the chip and/or antenna to the pill include inserting, implanting, tissue gluing, epoxy gluing, gluing, laminating, sewing, hot pressing, shrink wrapping, vacuum wrapping, soldering, encasing in plastic, rolling into, molding, strapping, stamping, retrofitting, embossing, hooking, attaching by VELCRO™ or the like, intertwining clusters of balls, attaching by TEFLON™, meshing, emulsifying, suspending, floating or mixing in liquids, gases, slurries and the like, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, for example, a drug delivery reservoir, biosensor, temperature sensor, and the like, and entrapping the chip and/or antenna segments with an attachment layer.

The components of the antenna structure, including chip, substrate, conductors, and adhesives, can be made entirely of ingestible or digestible materials. Examples of substrates which can be used include protein films and papers, e.g. gelatin, wheat, soy, whey, and rice papers, polysaccharide films such as cellulose derivatives and blends, ethyl cellulose, or sugars, lipids, such as wax or paraffin, among others. Edible gold and silver among other materials can be used for conductors and circuit printing. They can be provided in many forms, such as slurries, inks, or foils.

The larger effective area provided by the first antenna configurations discussed above provides a longer range for the signal transmission and reception. The signal range can be up to about 1 cm to about 3 m, more specifically up to about 5 cm to about 50 cm, most specifically up to about 15 cm.

In some cases, it may be desirable for the RFID antenna not to deploy at the same time the pill dissolves. One way to add a delay is to coat the antenna with a material which does not dissolve in the same environment as the pill material. For instance, cellulose acetate phthalate can be used as an enteric coating to coat the transmitter, causing it not to dissolve in the acidic environment of the stomach, but to dissolve in the small intestine. Because the onboard battery is not activated until it becomes wet, the transmitter will not begin signal transmission until the coating dissolves.

In some embodiments, more than one transmitter can be used in a single pill. This increases the likelihood that the pill will be detected by the receiver. Also, if the transmitters are located at different depths in the pill, or coated with different substances, this can give valuable information. For instance, if one transmitter is configured to begin transmission when it enters the stomach, and another is configured to begin transmission when it enters the small intestine, this can give an indication of motility by tracking how long it takes for the pill to travel from the stomach to the small intestine.

For optimum performance, antennas that are used for wave propagation, such as is used in RFID applications, are designed with impedances that match the impedance of the signaling medium. The impedance can be adjusted to match by adjusting the value of resistors and capacitors in the antenna. In free space, the impedance is approximately 377Ω, and antennas are matched accordingly.

Inside the body, the index of refraction is approximately 9, yielding a much higher impedance of about 3393Ω. Adjustments need to be made to the antenna in order to optimize it for use in the body. This can be done by scaling the resistances and capacitances in the antenna to yield an impedance which matches the impedance in the signaling medium, such as the body.

Other configurations of interest include, but are not limited to: those described in copending PCT application serial no. PCT/US2006/016370; the disclosure of which is herein incorporated by reference.

As reviewed above, the circuitry that drives the identifier may include a number of different functional blocks, e.g., signal generation blocks, activation blocks, transmitter blocks, etc. In certain embodiments, these functional blocks are provided in the form of an integrated circuit, where the integrated circuits of these embodiments include a number of distinct functional blocks, i.e., modules, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention are distinct from hybrid integrated circuits, which are miniaturized electronic circuits constructed of individual semiconductor devices, as well as passive components, bonded to a substrate or circuit board.

The support with which the circuit is associated, e.g., by being present on surface of the support or integrated, at least partially, inside of the support, may be any convenient support, and may be rigid or flexible as desired. As the support is intraluminal sized, its dimensions are such that it can be positioned inside of a physiological lumen, e.g., inside of a vessel, such as a cardiac vessel, e.g., a vein or artery. In certain embodiments, the intraluminal sized integrated circuits have a size (e.g., in terms of surface area of largest surface) of between about 0.05 mm$^2$ and about 5 mm$^2$, such as between about 1.125 mm$^2$ and about 2.5 mm$^2$, and including about 1.5 mm$^2$. The supports of the integrated circuits can have a variety of different shapes, such as square, rectangle, oval, and hexagon, irregular, etc.

The transmitter component may take a number of different configurations, e.g., depending on the type of signal that is generated and is to be emitted. In certain embodiments, the transmitter component is made up of three or more transmission elements, e.g., electrodes, where the electrodes may be coupled to antenna elements, e.g., wires, where desired. In certain embodiments, the signal is transmitted either by one or two electrodes, which may or may not be part of an antenna, e.g., coupled to a wire.

Depending on a given embodiment, the signal may or may not be modulated. For example, in certain embodiments the frequency of the signal may be held constant. In yet other embodiments, the signal may be modulated in some manner, e.g., via carrier based modulate schemes, ultra-wide band (or time domain based) modulation schemes, etc. Information can be encoded in various ways, generally by modulating (varying) some property of the transmitted signal, such as frequency, amplitude, phase, or any combination thereof. Modulation techniques known in the art may be employed.

In general, information can be transmitted using analog or digital techniques. "Analog techniques" refers generally to instances in which the modulated property is varied in different degrees, with the degree of variation being correlated to a value representing the information to be transmitted. For instance, an oscillator can be designed to operate over some range of frequencies. "Digital techniques" refers generally to instances in which the information to be transmitted is represented as a sequence of binary digits (bits), and the signal is modulated based on the bit stream. For instance, an oscillator can be designed to operate at least two different frequencies, with one frequency corresponding to bit value 0 and another frequency corresponding to bit value 1. In embodiments of the present invention, either analog techniques, digital techniques, or a combination thereof can be used to transmit information. In addition, various types of modulation may be implemented. For instance, in one embodiment, frequency modulation is used. An oscillator can be a voltage-controlled oscillator (VCO), an oscillator circuit in which the oscillation frequency depends on an applied voltage. Control logic can supply an appropriate voltage (e.g., reflecting the value of the measurement data, M), and the frequency of the signal indicates the value of the data. In another embodiment, amplitude modulation is used; for instance, the amplitude of the driving signals $\phi$ and $/\phi$ can be varied, or the positive and negative rails of the driver circuit (e.g., V+ and V−) can be varied to control the amplitude. In another embodiment, phase modulation is used. For instance, in digital signal transmission, one phase corresponds to bit value 0, an opposite phase corresponds to bit value 1, and the phase shifts represent transitions. An oscillator can include a switch circuit that either directly connects or cross-connects the driving signals $\phi$ and $/\phi$ to the inputs of a driver circuit.

In some embodiments, the transmitter may transmit a "packet" that includes a unique identifier for the identifier, which in turn is for the composition with which the identifier is associated. The unique identifier may also provide information from the remote device (e.g., the identity of the active agent (i.e., annotation information)). Other techniques for distinguishing different signals may also be used, including: operating different transmitters in different frequency bands, allowing each transmitter to be identified by its frequency and/or configuring different transmitters to transmit at different (and known) times, allowing the transmitter to be identified by when it transmits.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

In certain embodiments, the signal generation element includes circuitry, as developed in more detail below, which produces or generates the signal that is then transmitted as described above. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

Figure 3:
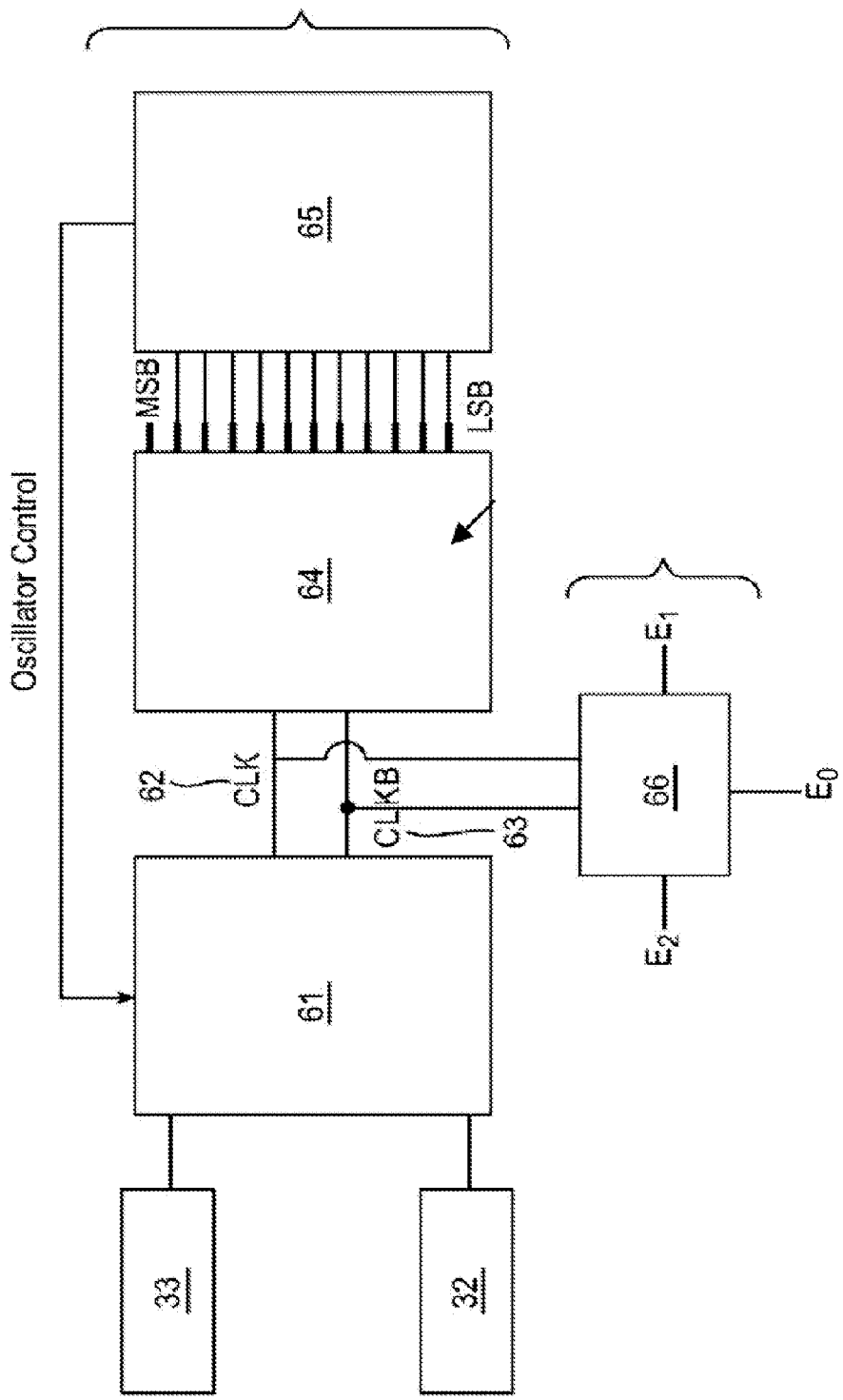
FIG. 3 provides detail of certain implementations of an electronic circuit of an embodiment of the invention.

FIG. 3 shows the detail of one implementation of an electronic circuit that can be employed in an identifier according to the present invention. On the left side are the two battery electrodes, metal 1 and metal 2 (32 and 33). These metals, when in contact with an electrolyte (produced upon contact with target site fluid, either alone or in combination with dried conductive medium precursor, as reviewed above), form a battery that provides power to an oscillator 61, in this case shown as a schematic. The metal 1 32 provides a low voltage, (ground) to the oscillator 61. Metal 2 33 provides a high voltage ($V_{high}$) to the oscillator 61. As the oscillator 61 becomes operative, it generates a clock signal 62 and an inverted clock signal 63, which are opposites of each other. These two clock signals go into the counter 64 which simply counts the number of clock cycles and stores the count in a number of registers. In the example shown here, an 8 bit counter is employed. Thus, the output of counter 64 begins with a value of "00000000," changes to "00000001" at the first clock cycle, and continues up to "11111111." The 8-bit output of counter 64 is coupled to the input of an address multiplexer (mux) 65. In one embodiment, mux 65 contains an address interpreter, which can be hard-wired in the circuit, and generates a control voltage to control the oscillator 61. Mux 65 uses the output of counter 64 to reproduce the address in a serial bit stream, which is further fed to the signal-transmission driving circuit. Mux 65 can also be used to control the duty-cycle of the signal transmission. In one embodiment, mux 65 turns on signal transmission only one sixteenth of the time, using the clock counts generated by counter 64. Such a low duty cycle conserves power and also allows other devices to transmit without jamming their signals. The address of a given chip can be 8 bits, 16 bits or 32 bits. Typically, more than 8 bits will be used in a product because there are so many different types of pharmaceuticals. Each pharmaceutical will have its own specific address.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 which can drive the electrodes to impose a differential potential to the solution, drive an oscillating current through a coil to generate a magnetic signal, or drive a single electrode to push or pull charge to or from the solution. In this manner, the device broadcasts the sequence of 0's and 1's which constitute the address stored in mux 65. That address would be broadcast repeatedly, and would continue broadcasting until metal 1 or metal 2 (32 and 33) is consumed and dissolved in the solution, when the battery no longer operates.

As reviewed above, the signal may vary significantly. In certain embodiments, the signal is a phase-shift-keyed signal. For example, the signal may be a 32 bit code that is phase-shift-keyed as a stream of sub-bits. In such embodiments, each sub-bit in the encoded bit stream may be implemented as a specific sequence of driver logic vectors in 16 different ways: 4 different drive patterns and 4 different data rates. For example, the code may consist of a 16-bit clock signal, a 4-bit preamble, an 8-bit payload, and a 4-bit disable sequence when all of the electrodes are off. 4 codes possible are:

| Code Designation | Bit Sequence |
|---|---|
| 0 | 0000 0000 0000 1010 1100 1100 (Z)x104 |
| 1 | 0000 0000 0000 1010 0001 0001 (Z)x104 |
| 2a | 0000 0000 0000 1010 1010 0101 (Z)x104 |
| 2b | 0000 0000 0000 1010 1110 1010 (Z)x104 |

In one bipolar coding scheme, the encoding scheme maps a code bit to an encoded sub-bit sequence, with the sequence repeated 16 times for a code bit 1, and the negation of the sequence repeated 16 times for a code bit 0

| Encoding Scheme | Code Bit 0 | Code Bit 1 |
|---|---|---|
| PSK-16 | CCCCCCCCCCCCCCCC = (C)x16 | ~(CCCCCCCCCCCCCCCC) = (~C)x16 |

The encoded sub-bit stream may be modulated to the 3 electrodes in 16 different ways sequentially, which are listed below:

| Electrode | C |
|---|---|
| Monopole-2 | |
| E0 | 0011 |
| E1 | 0011 |
| E2 | 0011 |
| CLK | 1010 |
| E0/E1-2 | |
| E0 | 0011 |
| E1 | 1100 |
| E2 | ZZZZ |
| CLK | 1010 |
| E0/E2-2 | |
| E0 | 0011 |
| E1 | ZZZZ |
| E2 | 1100 |
| CLK | 1010 |
| E1/E2-2 | |
| E0 | ZZZZ |
| E1 | 0011 |
| E2 | 1100 |
| CLK | 1010 |
| Beacon-3 | |
| E0 | 11ZZ00 |
| E1 | 0011ZZ |
| E2 | ZZ0011 |
| CLK | 101010 |
| E0/E1-4 | |
| E0 | 00001111 |
| E1 | 11110000 |
| E2 | ZZZZZZZZ |
| CLK | 10101010 |
| E0/E2-4 | |
| E0 | 00001111 |
| E1 | ZZZZZZZZ |
| E2 | 11110000 |
| CLK | 10101010 |
| E1/E2-4 | |
| E0 | ZZZZ |
| E1 | 0000 |

-continued

| Electrode | C |
|---|---|
| E2 | 1111 |
| CLK | 1010 |
| | Beacon-6 |
| E0 | 1111ZZ0000ZZ |
| E1 | 00ZZ1111ZZ00 |
| E2 | ZZ0000ZZ1111 |
| CLK | 101010101010 |
| | E0/E1-6 |
| E0 | 000000111111 |
| E1 | 111111000000 |
| E2 | ZZZZZZZZZZZZ |
| CLK | 101010101010 |
| | E0/E2-6 |
| E0 | 000000111111 |
| E1 | ZZZZZZZZZZZZ |
| E2 | 111111111111 |
| CLK | 101010101010 |
| | E1/E2-6 |
| E0 | ZZZZZZZZZZZZ |
| E1 | 000000111111 |
| E2 | 111111000000 |
| CLK | 101010101010 |
| | Beacon-12 |
| E0 | 111111111ZZ0000000000ZZ11 |
| E1 | 0000ZZ1111111111ZZ000000 |
| E2 | ZZ0000000000ZZ1111111111 |
| CLK | 101010101010101010101010 |
| | E0/E1-12 |
| E0 | 000000000000111111111111 |
| E1 | 111111111111000000000000 |
| E2 | ZZZZZZZZZZZZZZZZZZZZZZZZ |
| CLK | 101010101010101010101010 |
| | E0/E2-12 |
| E0 | 000000000000111111111111 |
| E1 | ZZZZZZZZZZZZZZZZZZZZZZZZ |
| E2 | 111111111111000000000000 |
| CLK | 101010101010101010101010 |
| | E1/E2-12 |
| E0 | ZZZZZZZZZZZZZZZZZZZZZZZZ |
| E1 | 000000000000111111111111 |
| E2 | 111111111111000000000000 |
| CLK | 101010101010101010101010 |

On a particular chip with a particular code, the different modulation schemes are output in sequence. The code may be output in each of the 16 modulation schemes, with a dormant state, where all the outputs are disabled, for a set duration between. The output sequence may be:
Monopole-2
E0/E1-2
E0/E2-2
E1-E2-2
Beacon-3
E0/E1-4
E0/E2-4
E1-E2-4
Beacon-6
E0/E1-6
E0/E2-6
E1-E2-6
Beacon-12
E0/E1-12
E0/E2-12
E1-E2-12

The present invention also allows the possibility that, where appropriate, each pharmaceutical batch can be provided with a batch specific address. This allows identification of where the pill was made, when the pill was made, and in what batch it was made. In some cases, each pill will have a unique identifier. This would be particularly useful when drugs are more likely to be subsequently stolen or used illicitly, and thus should be tracked, or where questions of contamination may arise.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 having at least three signal transmission elements, e.g., electrodes (shown in the figure as $E_0$, $E_1$ and $E_2$) which can drive the signal transmission element in a variety of formats, e.g., monopole, dipole, etc., to provide a multidirectional transmission of the identifying signal. In this manner, the device broadcasts the sequence of 0's and 1's which constitute the address stored in mux 65. The address (i.e., identifying signal) may be broadcast repeatedly, as desired. Other configurations for the signal generation component are of course possible.

Other configurations of interest include, but are not limited to: those described in copending PCT application serial no. PCT/US2006/016370; the disclosure of which is herein incorporated by reference.

Other configurations for the circuitry are of course possible. Other configurations of interest include, but are not limited to, those described in PCT application serial no. PCT/US2006/016370 filed on Apr. 28, 2006 and titled "Pharma-Informatics System"; PCT application serial no. PCT/US2007/022257 filed on Oct. 17, 2007 and titled "In-vivo Low Voltage Oscillator for Medical Devices"; PCT application serial no. PCT/US US2007/82563 filed on Oct. 25, 2007 and titled "Controlled Activation Ingestible Identifier"; U.S. patent application Ser. No. 11/776,480 filed Jul. 11, 2007 entitled "Acoustic Pharma Informatics System"; and PCT application serial no. PCT/US2008/52845 filed on Feb. 1, 2008 and titled "Ingestible Event Marker Systems"; the disclosures of which applications (and particularly signal generation components thereof) are herein incorporated by reference.

The identifiers may be fabricated using any convenient processing technology. In certain embodiments, planar processing protocols are employed to fabricate power sources having surface electrodes, where the surface electrodes include at least an anode and cathode at least partially on the same surface of a circuitry support element. In some embodiments, the power source can comprise a battery. In certain embodiments, planar processing protocols are employed in a wafer bonding protocol to produce a battery source. Planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electrodeposition (e.g., electroplating), cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

In certain embodiments, the identifier may be one that is programmable following manufacture, in the sense that the signal generated by the identifier may be determined after the identifier is produced. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. 20050131281, and the like, the disclosures of which are herein incorporated by reference. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference.

The identifier of certain embodiments includes a memory element, where the memory element may vary with respect to its capacity. In certain embodiments, the memory element has a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of active agent, etc.

Optional Physiologically Acceptable Carrier Component

Identifiers of the invention that include RFID antennas as described above may be present in (i.e., combined with) a physiologically acceptable carrier component, e.g., a composition or vehicle that aids in ingestion of the identifier and/or protects the identifier until it reaches the target site of interest. As used herein, a physiologically acceptable carrier component refers to a composition, which may be a solid or fluid (e.g., liquid), which is ingestible.

Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

Other components suitable for use in the formulations of the present invention can be found in Remington's Pharmaceutical Sciences, Mace Publishing Company, Philadelphia, Pa., 17th ed. (1985).

Optional Active Agent

In certain embodiments, the identifier is not associated with a pharmaceutically active agent. As such, the identifier, and any carrier or other component that make up the ingestible event marker, do not include an active agent.

In yet other embodiments, the identifier is associated with an active agent, e.g., where the active agent is present in the carrier composition that includes the identifier. In some embodiments, the signal generation element can be stably associated with an active agent. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The active agent may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

A variety of manufacturing protocols may be employed to produce compositions as described above, e.g., where an identifier is present in pharmaceutically acceptable carrier or vehicle, where the carrier or vehicle may further include one or more active agents. In manufacturing such compositions, an identifier is stably associated with the pharmaceutical dosage form in some manner. By stably associated is meant that the identifier and the dosage form do not separate from each other, at least until administered to the subject in need thereof, e.g., by ingestion. The identifier may be stably associated with the pharmaceutical carrier/active agent component of the composition in a number of different ways. In certain embodiments, where the carrier/active agent component is a solid structure, e.g., such as a tablet or pill, the carrier/active agent component is produced in a manner that provides a cavity for the identifier. The identifier is then placed into the cavity and the cavity sealed, e.g., with a biocompatible material, to produce the final composition. For example, in certain embodiments a tablet is produced with a die that includes a feature which produces a cavity in the resultant compressed tablet. The identifier is placed into the cavity and the cavity sealed to produce the final tablet. In a variation of this embodiment, the tablet is compressed with a removable element, e.g., in the shape of a rod or other convenient shape. The removable element is then removed to produce a cavity in the tablet. The identifier is placed into the cavity and the cavity sealed to produce the final tablet. In another variation of this embodiment, a tablet without any cavity is first produced and then a cavity is produced in the tablet, e.g., by laser drilling. The identifier is placed into the cavity and the cavity sealed to produce the final tablet. In yet other embodiments, a tablet is produced by combining the identifier with subparts of the tablet, where the subparts may be pre-made subparts or manufactured sequentially. For example, in certain embodiments tablets are produced by first making a bottom half of the tablet, placing the signal generation element on a location of the bottom half of the tablet, and then placing top portion of the tablet over the bottom half and signal generation element to produce the final desired composition. In certain embodiments, a tablet is produced around an identifier such that the identifier is located inside of the produced tablet. For example, an identifier, which may or may not be encapsulated in a biocompatible compliant material, e.g., gelatin (to protect the signal generation element), is combined with carrier/active agent precursor, e.g., powder, and compressed or molded into a tablet in a manner such that the identifier is located at an internal position of the tablet. Instead of molding or compressing, the carrier/active agent component is, in certain embodiments, sprayed onto an identifier in a manner that builds up the tablet structure. In yet another embodiment, the active agent/carrier component precursor may be a liquid formulation which is combined with the identifier and then solidified to produce the final composition. In yet other embodiments, pre-made tablets may be fitted with an identifier by stably attaching an identifier to the tablet. Of interest are protocols that do not alter the properties of the tablet, e.g., dissolution etc. For example, a gelatin element that snap fits onto one end of a tablet and has an identifier integrated with it is employed in certain embodiments. The gelatin element is colored in certain embodiments to readily identify tablets that have been fitted with the signal generation element. Where the composition has an active agent/carrier composition filled capsule configuration, e.g., such as a gelatin capsule filled configuration, an identifier may be integrated with a capsule component, e.g., top or bottom capsule, and the capsule filled with the active agent/carrier composition to produce the final composition. The above reviewed methods of manufacture are merely illustrative of the variety of different ways in which the compositions of the invention may be manufactured.

In certain embodiments, the identifiers are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact.

Systems

Also provided are systems that include the subject compositions. Systems of the subject invention include, in certain embodiments, an ingestible or implantable event marker comprising one or more devices that include a RFID antenna of the invention, e.g., an identifier as reviewed above, as well as a signal detection component, e.g., in the form of a receiver. The signal detection component may vary significantly depending on the nature of the signal that is generated by the signal generation element of the composition, e.g., as reviewed above.

Signal receivers of systems of embodiments of the invention are those that are configured to receive a signal from an identifier, e.g., to receive a signal emitted by an identifier upon contact of the identifier with the target physiological site following ingestion of the identifier. The signal receiver may vary significantly depending on the nature of the signal that is generated by the signal generation element, e.g., as reviewed below. As such, the signal receiver may be configured to receive a variety of different types of signals, including but not limited to: RF signals, magnetic signals, conductive (near field) signals, acoustic signals, etc., as indicated above. In certain embodiments, the receiver is configured to receive a signal conductively from another component, e.g., the identifier, such that the two components use the body of the patient as a communication medium. As such, the signal that is transferred between identifier and the receiver travels through the body, and requires the body as the conduction medium. The identifier emitted signal may be transmitted through and received from the skin and other body tissues of the subject body in the form of electrical alternating current (a.c.) voltage signals that are conducted through the body tissues. As a result, such embodiments do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject. In certain embodiments, the signal detection component is one that is activated upon detection of a signal emitted from an identifier. In certain embodiments, the signal receiver is capable of (i.e., configured to) simultaneously detecting multiple different signals, e.g., 2 or more, 5 or more, 10 or more, etc.

The signal receiver may include a variety of different types of signal receiver elements, where the nature of the receiver element necessarily varies depending on the nature of the signal produced by the signal generation element. In certain embodiments, the signal receiver may include one or more electrodes (e.g., 2 or more electrodes, 3 or more electrodes, and/or includes multiple, e.g., 2 or more, 3 or more, 4 or more pairs of electrodes, etc.) for detecting signal emitted by the signal generation element. In certain embodiments, the receiver device will be provided with two electrodes that are dispersed at a distance, e.g., a distance that allows the electrodes to detect a differential voltage. This distance may vary, and in certain embodiments ranges from about 0.1 to about 5 cm, such as from about 0.5 to about 2.5 cm, e.g., about 1 cm. In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element. In certain embodiments, multiple pairs of electrodes (e.g., as reviewed above) are provided, for example to increase detection probability of the signal.

The signal receivers of interest include both external and implantable signal receivers. In external embodiments, the signal receiver is ex vivo, by which is meant that the receiver is present outside of the body during use. Where the receiver is implanted, the signal receiver is in vivo. The signal receiver is configured to be stably associated with the body, e.g., either in vivo or ex vivo, at least during the time that it receives the emitted signal from the IEM.

Signal receivers of interest include, but are not limited to, those receivers disclosed in: PCT application serial no. PCT/US2006/016370 filed on Apr. 28, 2006 and titled "Pharma-Informatics System"; and PCT application serial no. PCT/US2008/52845 filed on Feb. 1, 2008 and titled "Ingestible Event Marker Systems"; the disclosures of which applications (and particularly signal receiver components thereof) are herein incorporated by reference.

In certain embodiments, the signal receiver is configured to provide data of a received signal to a location external to said subject. For example, the signal receiver may be configured to provide data to an external data receiver, e.g., which may be in the form of a monitor (such as a bedside monitor), a computer (e.g., PC or MAC), a personal digital assistant (PDA), phone, messaging device, smart phone, etc. In one embodiment, if a signal receiver failed to detect a signal indicating that a pill had been ingested, the signal receiver could transmit a reminder to take the pill to the subject's PDA or smart phone, which could then provide a prompt to the user to take the medication, e.g., a display or alarm on the PDA, by receiving a phone call on the smart phone (e.g., a recorded message) etc. The signal receiver may be configured to retransmit data of a received signal to the location external to said subject. Alternatively, the signal receiver according may be configured to be interrogated by an external interrogation device to provide data of a received signal to an external location.

As such, in certain embodiments the systems include an external device which is distinct from the receiver (which may be implanted or topically applied in certain embodiments), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, smart phones, home computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Methods

Aspects of the invention further include methods of using in-body devices that include RFID antennas of the invention. Generally, methods of the invention will include placing the in-body device in some manner in the body of the subject, e.g., by implanting the device in a subject, by ingesting the device, etc. The devices may be employed with a variety of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain embodiments, the subjects will be humans. Following placement of the devices in the body of a subject, the devices are employed for a variety of purposes, e.g., to sense one or more physiological parameters, to deliver one or more therapies, to mark a personal event of interest, etc.

In certain embodiments, the in-body devices are ingestible devices, where the RFID antenna is part of an identifier of the device. In such embodiments, the identifier is ingested and a signal emitted by the identifier is detected, e.g., with a receiver as described above. Such methods are further described in PCT application serial no. PCT/US2006/016370 filed on Apr. 28, 2006 and titled "Pharma-Informatics System"; and PCT application serial no. PCT/US US2008/52845 filed on Feb. 1, 2008 and titled "Ingestible Event Marker Systems"; the disclosures of which applications (and particularly signal receiver components thereof) are herein incorporated by reference.

Utility

Devices that include the RFID antennas of the invention may be employed in a variety of different applications, including both therapeutic and non-therapeutic applications. Specific applications of interest include, but are not limited to: those applications described in PCT application serial no. PCT/US2006/016370 filed on Apr. 28, 2006 and titled "Pharma-Informatics System"; and PCT application serial no. PCT/US US2008/52845 filed on Feb. 1, 2008 and titled "Ingestible Event Marker Systems"; the disclosures of which applications (and particularly signal receiver components thereof) are herein incorporated by reference.

IEM in body devices of the invention may be employed in a variety of different applications, which applications may be both medical and non-medical in nature. Different illustrative applications are now reviewed in greater detail below.

Certain applications involve the use of IEMs by themselves to mark a personal event of interest, e.g., onset of a physiological parameter (such as a symptom(s) of interest), onset of an activity, etc. For example, in certain embodiments, event markers are employed to mark the onset of a symptom of interest. In such instances, when an individual becomes aware of a symptom of interest, e.g., begins to feel flushed, nauseous, excited, etc., e.g., the individual may ingest an IEM to mark the occurrence of the symptom of interest. For example, the patient may begin to not feel well, and ingest an event marker in response to this ill feeling. Upon ingestion, the marker sends a signal to a receiver, which may then record receipt of the signal for further use, e.g., to combine with physiological data, etc. In certain embodiments, the received signal is employed to provide context for any physiological data that is obtained from the patient, e.g., by sensors on the receiver, from an implantable recorder, etc.

Another symptom of interest is pain. In these embodiments, the ingestible event marker may be employed as a pain marker. For example, in the case where a patient is being monitored for pain, if a patient feels no pain, the patient may ingest a first type of marker. If the patient feels pain, the patient may ingest a second type of marker. Different types of markers may be differentiated, such as color coded, where desired, to assist in their identification and proper use by the patient. For example, markers to be ingested when the patient does not feel pain may be color coded blue, while markers that are to be ingested when the patient does have pain may be color coded yellow. In another embodiment, instead of having different types of markers, a protocol may be employed in which the number of markers ingested, and therefore the signal obtained, e.g., from a single marker or two or more markers, is employed to denote a scale of the symptom of interest, such as pain. For example, if an individual is having intense pain, the individual takes four of the positive pain marker pills at the same time, while in response to mild pain the individual may take only one marker.

In such embodiments, the onset of the symptom of interest, as marked by the ingestion of the event marker and detection of the signal by the receiver, may be employed as relevant point at which to begin recording one or more physiological parameters of interest, e.g., by using an implantable physiological monitor. In these instances, the emitted signal from the marker is received by the receiver, which then causes a physiological parameter recorder (such as a Reveal® Plus Insertable Loop Recorder (ILR), Medtronic Corporation) to begin recording data and saving the data, e.g., for later use. For example, an implantable physiological parameter recorder may have only a limited possible amount of time for recording (such as 42 minutes). In such situations, the data may be automatically overwritten unless somehow flagged or marked for protection. In the present methods, an IEM may be ingested to mark the onset of a symptom of interest, as perceived by the patient, and the receiver upon receipt of the signal may act with the recorder to protect the data obtained around the time of the signal (after, or even some time before) to be protected and not overwritten. The system may be further configured to work in response not only to the ingestion of the event marker, but also in response to physiological sensed parameters, e.g., pH. As such, the methods find use as an event recorder in terms of flagging a diagnostic stream of information, and protecting it from being overwritten, so a physician can look at it at a later date.

In certain embodiments, the event marker provides the context for interpreting a given set of physiological data at a later time. For example, if one is employing an activity sensor and one co-administers an event marker with a particular drug, one can note any change in activity that is brought about by that drug. If a drop in activity is observed after a person takes both the event marker and a drug, the drop indicates the drug is probably causing the person to reduce their activity, e.g., by making them feel sleepy or actually causing them to fall asleep. Such data may be employed to adjust the dose of a drug or be the basis for a decision to switch to an alternative medication.

In certain embodiments the event marker is employed to construct a database of multiple events. Such a database may be employed to find commonality between the multiple marked events. Simple or complex protocols for finding commonality among multiple marked events may be employed. For example, multiple events may be averaged. Alternatively techniques such as impulse response theory may be employed, where such techniques provide information on what exactly are the common features in a set of multiple sensor streams that are tied to a particular event.

The IEM systems of the invention enable one to use subjective symptoms, such as "I'm feeling funny," to impart context and background to obtained objective measures of what is occurring physiologically. For example, if every time a subject felt abnormal they took an event marker, one could reference a database of the objective sensor data, and find common features in the database. Such an approach may be employed to discover the underlying causes of the subjective feeling. For example, such an approach may be employed to determine that every time a patient is feeling "funny", there is an associated change in their blood pressure, and the link between a subjective symptom and objective physiological data can be used in their diagnosis. As such, a generalizable event marker brings context to discrete data from any other source. Therefore, use of the oral medication event markers can provide context for any other associated health monitoring information or health event.

In certain embodiments, the event marker can be an alert marker, such that ingestion of the marker causes an alarm signal to be sent from the patient, e.g., indicating that the patient needs medical assistance. For example, when a patient feels an onset of a symptom of interest, such as chest pain, shortness of breath, etc., the patient may ingest an event marker. The signal emitted from the event marker may be received by the receiver, which may then cause an alarm to be generated and distributed to a medical professional.

In certain embodiments, the event marker is employed to instigate or start a therapeutic action, e.g., activate an implantable pulse generator to deliver electrical therapy, activate an implanted drug delivery device to administer a dosage of drug, activate a physiological sensor to begin acquiring data, etc. For example, where a patient has a neural stimulator for treating migraines, upon perception of the onset of aura, the patient could ingest an IEM. The emitted signal would then activate neural stimulator into stimulus mode, and thereby cause the implant to deliver therapy. Alternatively, if one has an implanted drug delivery device, e.g., a device that delivers an oncotic agent, ingestion of the IEM could cause the implanted device to deliver the active agent.

In certain embodiments, the event marker is employed to deliver information to an implanted medical device in the patient. For example, an ingestible event marker may send a signal that includes updated data for an implanted medical device, such as firmware upgrade data for an implantable pulse generator, e.g., a pace maker. In such instances, the signal may include the upgrade code which is broadcast from the IEM conductively to the medical device, where upon receipt of the signal and code, the firmware of the medical device is upgraded.

Other applications where event markers may be employed by themselves is to mark or note the start of non-medical personal event, such as a commute time, the start of an exercise regimen, sleep time, smoking (e.g., so one can log how much one smokes) etc.

As indicated above, embodiments of the invention are characterized in that the event markers are co-ingested with another composition of matter, e.g., a pharmaceutical composition, food, etc, where the event marker may or may not be present in the same composition as the co-ingested matter. For example, the event markers may be employed to track ingesting a pharmaceutical agent, where one co-administers the marker with the drug of interest. Applications where co-administration of a drug and marker is of interest include, but are not limited to, clinical studies, titration of medicine, e.g., blood pressure medicine, etc. Where desired, the IEM could be provided as just another pill to indicate when a refill is needed from the pharmacy.

Instead of co-ingesting the event marker with another composition, e.g., a drug, food, etc., the marker and the other composition may be compounded together, e.g., by the end user. For example, an IEM in the form of a capsule can be opened by the end user and filled with a pharmaceutical composition. The resultant compounded capsule and active agent may then be ingested by the end user. Instead of an end user, the pharmacist or a health care provider may perform the compounding step.

In yet other embodiments, the marker is present already compounded with the other composition at the source of manufacture of the other composition, e.g., the manufacturer or producer of a pharmaceutical composition. An example of such compositions includes those described in PCT application serial no. PCT/US2006/016370; the disclosure of which is herein incorporated by reference.

In certain embodiments, the IEMs of the invention are employed to allow one to look at, on an individual basis, what a given result is with respect to what drugs an individual is taking versus their impact on indicators that correlate to the desired effect. For example, where a given patient is prescribed a regimen of multiple pharmaceutical agents and there are multiple different physiological parameters that are monitored as indicators of how the patient is responding to the prescribed therapeutic regimen, a given drug as marked by a given marker can be assessed in terms of its impact on one or more of the physiological parameters of interest. Following this assessment, adjustments can be made accordingly. In this manner, automation may be employed to tailor therapies based on individual responses. For example, where a patient is undergoing oncotic therapy, the event marker can be used to provide real time context to obtained physiological parameter data. The resultant annotated real time data can be used to make decisions about whether or not to continue therapy, or change to a new therapy.

In certain embodiments, a dosing event (as marked by the IEM) is correlated with sensor data to develop a profile for how a given drug acts, e.g., in terms of a pharmacokinetic and/or pharmacodynamic model. Sensors are employed with the IEM marking of the dosing event to obtain a pharmacokinetic model. Once a pharmacokinetic model is derived, one can use the dosing event to drive that model and predict serum drug levels and response. One might find, as determined from various sensors, that a patient is not responding well to therapy at a particular time. One might look back at the pharmacokinetic model to find that the levels of the therapeutic drug in the blood are low when the patient is not responding well, based on symptoms and/or objective physiological data. This data can then be used to make a determination to increase the dosing frequency or increase the dose level at a given dosing event. The event marker can therefore provide a way to develop a pharmacokinetic and/or pharmacodynamic model and then apply it to optimize patient therapy.

Where the IEMs are co-administered with a pharmaceutical agent, e.g., as two separate compositions or a single composition (as described above), the systems of the invention, enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians.

In certain embodiments, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another embodiment, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another embodiment, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimes. In another embodiment, one can combine information from a sensor that measures uterine contractions (e.g. with a strain gauge) and that also monitors fetal heart rate, for use as a high-risk pregnancy monitor.

In certain embodiments, the subject specific information that is collected using the systems of the invention may be transmitted to a location where it is combined with data from one or more additional individuals to provide a collection of data which is a composite of data collected from 2 or more, e.g., 5 or more, 10 or more, 25 or more, 50 or more, 100 or more, 1000 or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from 100 different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another embodiment, doctors can also be granted access to a manipulation of the composite data to see how their patients are matching up with patients of other doctors, and obtain useful information on how real patients respond to a given therapeutic treatment regiment. Additional functionalities can be provided to the groups given access to the composite data, where such functionalities may include, but are not limited to: ability to annotate data, chat functionalities, security privileges, etc.

The inventive pharmacokinetic model allows for drug dosing regimens to be adjusted in real time in response to varying serum levels in the body. The pharmacokinetic model can predict or measure the serum level of a given medication in the body. This data can then be used to calculate when the next dose of medication should be taken by the patient. An alarm can be triggered at that time to alert the patient to take a dose. If the serum level remains high, an alarm can be triggered to alert the patient not to take the next dose at the originally prescribed time interval. The pharmacokinetic model can be used in conjunction with a medication ingestion monitoring system that includes an IEM, such as that described above. Data from this system can be incorporated into the model, as well as population data, measured data, and data input by the patient. Utilizing data from multiple sources, a very powerful and accurate tool can be developed.

In some embodiments, the data gathered by the receiver can be used directly by the pharmacokinetic model to determine when a medication was administered, what medication it was and in what amount. This information can be used to calculate an estimate of the serum level of the medication in the patient. Based on the calculated serum level, the pharmacokinetic model can send an alert to the patient to say either that the serum level is too high and is near or above the toxic level, or that the serum level is too low and they should take another dose. The pharmacokinetic model can be run on the implanted receiver itself or on an external system which receives data from the implanted receiver.

A simple form of the pharmacokinetic model can assume that every patient is the same, and use average population data to model the serum level. A more complex and more accurate model can be obtained by inputting other information about the patient. This information can be inputted by the user, such as a physician, or gathered by the receiver from associated sensors. Information that can be used to adjust the model include other medications being taken, diseases the patient suffers from, patient's organ function, enzyme levels, metabolism, body weight, and age, among other factors. Information can also be inputted by the patient themselves, such as if they feel hypoglycemic, or have pain or dizziness. This can be used as further evidence to validate the predictions of the model.

Examples of food applications include the following. In certain disease conditions, such as diabetes, it can be important what a patient ate and when. In such instances, event markers of the invention are keyed or linked to the type of food a patient eats. For example, one can have a set of event markers for different food items, and one can co-administer them with the food items. From the resultant data, one can do a complete individual metabolic profile on an individual. One knows how many calories the patient is consuming. By obtaining activity and heart rate and ambient temperature versus body temperature data, one can calculate how many calories one is expending. As a result, guidance can be provided to the patient as to what foods to eat and when. Non disease patients may also track food ingestion in this manner. For example, athletes adhering to a strict training diet may employ IEMs to better monitor food ingestion and the effect of the food ingestion on one or more physiological parameters of interest.

As reviewed in the above discussion, IEM systems of the invention find use in both therapeutic and non-therapeutic applications. In therapeutic applications, the IEM may or may not be compounded with a pharmaceutically active agent. In those embodiments where the IEM is compounded with active agent, the resultant compounded composition may be viewed as a pharma-informatics enabled pharmaceutical composition.

In such pharma-informatics embodiments, an effective amount of a composition that includes an IEM and an active agent is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith. In some embodiments, the signal generation element is stably associated with one or more active agents.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc.; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention, where the composition includes an active agent, an identifier element and a pharmaceutically acceptable carrier. In certain embodiments where the identifier emits a signal in response to an interrogation, the identifier is interrogated, e.g., by a wand or other suitable interrogation device, to obtain a signal.

The obtained signal is then employed to determine historical information about the composition, e.g., source, chain of custody, etc.

In certain embodiments, a system is employed that is made up of a multiple different IEMs, e.g., 2 or more distinct IEMS, 3 or more distinct IEMS, 4 or more distinct IEMs, etc., including 5 or more, 7 or more, 10 or more distinct IEMs. The distinct IEMs may be configured to provide distinguishable signals, e.g., where the signals may be distinguishable in terms of nature of the signal itself, in terms of timing of emission of the signal, etc. For example, each IEM in such sets may emit a differently coded signal. Alternatively, each IEM may be configured to emit the signal at a different physiological target site, e.g., where each IEM is configured to be activated at a different target physiological site, e.g., where an first IEM is activated in the mouth, a second is activated in the esophagus, a third is activated in the small intestine and a fourth is activated in the large intestine. Such sets of multiple different distinguishable IEMs find use in a variety of different applications. For example, where one has the above described 4 IEM set, one can use the set in a diagnostic application to determine function of the digestive system, e.g., motility through the digestive tract, gastric emptying etc. For example, by noting when each IEM emits its respective signal, a plot of signal time may be generated from which information regarding digestive tract functioning may be obtained.

In another embodiment, one or more IEMs can be configured to be activated at a target site, wherein the target site is reached after a specified period of time. This embodiment can also be used to determine function and motility of the digestive system, e.g. to determine the time it takes to reach various locations of the digestive tract.

The present invention provides the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in copending PCT Application Serial No. PCT/US2006/016370; the disclosure of which is herein incorporated by reference.

Additional applications in which the subject systems find use include those described in U.S. Pat. No. 6,804,558, the disclosure of which is herein incorporated by reference. For example, the subject systems may be used in a medical information communication system which permits monitoring the performance of an implantable medical device (IMD) implanted within a body of a patient, monitoring the health of the patient, and/or remotely delivering a therapy to the patient through the IMD. A signal receiver of the invention, e.g., in an external format such as a bandage or implanted format, communicates with the IMD and is capable of bi-directional communication with a communication module, a mobile telephone and/or a Personal Data Assistant (PDA) located outside the patient's body. The system may comprise the IMD, the signal receiver with the communication module and/or a mobile telephone and/or a PDA, a remote computer system, and a communication system capable of bi-directional communication, where the communication module, the mobile telephone and/or the PDA are capable of receiving information from the IMD or relaying information thereto via the signal receiver, which is internal or external to the patient, as reviewed above.

Additional applications in which receivers of the invention may find use include, but are not limited to: fertility monitoring, body fat monitoring, satiety monitoring, satiety control, total blood volume monitoring, cholesterol monitoring, smoking detection, etc.

Kits

Also provided are kits that include one or more in-body devices containing RFID antennas of the invention. Kits may include one or more in-body devices, e.g., as described above, including ingestible and/or implantable event markers. In those embodiments having a plurality of in-body devices (e.g. ingestible event markers), such may be packaged in a single container, e.g., a single tube, bottle, vial, and the like, or one or more dosage amounts may be individually packaged such that certain kits may have more than one container of an in-body device. In certain embodiments the kits may also include a signal receiving element, or receiver, as reviewed above. In certain embodiments, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain ranges have been presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An ingestible event marker comprising:
an identifier operative to emit a signal when activated at a target site, wherein the identifier comprises a signal generation circuit comprising a radio frequency identification (RFID) antenna, wherein the signal generation circuit comprises a voltage controlled oscillator (VCO) and a digital control circuit coupled to the VCO, the digital control circuit assigned an address, the digital control circuit to control the VCO with a control signal associated with the address;

wherein the digital control circuit further comprises:
a digital counter circuit comprising an input portion coupled to the VCO and an output portion, wherein the VCO is operative to generate a first clock signal and a second clock signal, wherein the second clock signal is an inverted version of the first clock signal, and wherein the first and second clock signals are coupled to the digital counter circuit, wherein the digital counter circuit is operative to count a number of clock cycles received from the VCO, store the count in at least one register, and provide the count to the output portion of the digital counter circuit.

2. The ingestible event marker according to claim 1, wherein the identifier is activated upon contact with fluid at the target site.

3. The ingestible event marker according to claim 2, wherein the target fluid is stomach fluid.

4. The ingestible event marker according to claim 1, wherein the identifier comprises a power source.

5. The ingestible event marker according to claim 4, wherein the power source comprises a battery.

6. The ingestible event marker according to claim 4, wherein the power source comprises a Galvanic cell.

7. The ingestible event marker according to claim 1, wherein an input signal to the RFID antenna is provided by a reader.

8. The ingestible event marker according to claim 1, wherein an input signal to the RFID antenna is provided by a battery.

9. The ingestible event marker according to claim 1, wherein the identifier has a limited lifespan.

10. The ingestible event marker according to claim 1, wherein the RFID antenna is configured to conform to ingestible pill dimensions.

11. The ingestible event marker according to claim 1, wherein the RFID antenna has a first configuration prior to ingestion and a second configuration after ingestion.

12. The ingestible event marker according to claim 11, wherein the RFID antenna unfolds after ingestion.

13. The ingestible event marker according to claim 11, wherein the RFID antenna has a greater effective area in the second configuration than in the first configuration.

14. The ingestible event marker according to claim 1, wherein the identifier comprises an integrated circuit.

15. The ingestible event marker according to claim 1, further comprising an active agent stably associated with the signal generation circuit.

16. A system comprising:
(a) an ingestible event marker comprising an identifier operative to emit a signal when activated at a target site, wherein the identifier comprises a signal generation circuit comprising a radio frequency identification (RFID) antenna, wherein the signal generation circuit comprises a voltage controlled oscillator (VCO) and a digital control circuit coupled to the VCO, the digital control circuit assigned an address, the digital control circuit to control the VCO with a control signal associated with the address, wherein the digital control circuit further comprises:
a digital counter circuit comprising an input portion coupled to the VCO and an output portion, wherein the VCO is operative to generate a first clock signal and a second clock signal, wherein the second clock signal is an inverted version of the first clock signal, and wherein the first and second clock signals are coupled to the digital counter circuit, wherein the digital counter circuit is operative to count a number of clock cycles received from the VCO, store the count in at least one register, and provide the count to the output portion of the digital counter circuit; and
(b) a receiver configured to detect a signal produced by the signal generation circuit.

17. The system according to claim 16, wherein the receiver is an in vivo receiver.

18. The system according claim 16, wherein the receiver is an ex vivo receiver.

19. A method comprising:
administering to a subject an ingestible event marker comprising an identifier operative to emit a signal when activated at a target site, wherein the identifier comprises a signal generation circuit comprising a radio frequency identification (RFID) antenna, a voltage controlled oscillator (VCO) and a digital control circuit coupled to the VCO, the digital control circuit assigned an address;
generating a digital clock signal in response to activation of the identifier to vary the frequency of the VCO; and
controlling the VCO by the digital control circuit with a control signal associated with the address;
wherein controlling the VCO comprises:
generating a first clock signal and a second clock signal, wherein the second clock signal is an inverted version of the first clock signal, and wherein the first and second clock signals are coupled to a digital counter circuit comprising an input portion coupled to the VCO and an output portion;
counting by the digital counter circuit a number of clock cycles received from the VCO;
storing the count in at least one register; and
providing the count to the output portion of the digital counter circuit.

20. A kit comprising:
at least one ingestible event marker comprising an identifier operative to emit a signal when activated at a target site, wherein the identifier comprises a signal generation circuit comprising a radio frequency identification (RFID) antenna, wherein the signal generation circuit comprises a voltage controlled oscillator (VCO) and a digital control circuit coupled to the VCO, the digital control circuit assigned an address, the digital control circuit to control the VCO with a control signal associated with the address;
wherein the digital control circuit further comprises:
a digital counter circuit comprising an input portion coupled to the VCO and an output portion, wherein the VCO is operative to generate a first clock signal and a second clock signal, wherein the second clock signal is an inverted version of the first clock signal, and wherein the first and second clock signals are coupled to the digital counter circuit, wherein the digital counter circuit is operative to count a number of clock cycles received from the VCO, store the count in at least one register, and provide the count to the output portion of the digital counter circuit.

21. The kit according to claim 20, wherein the kit comprises a plurality of the ingestible event markers.

22. The kit according to claim 20, wherein the kit further comprises a receiver.

23. An in-body device comprising:
a radio frequency identification (RFID) antenna; and
an identifier operative to emit a signal when activated at a target site, wherein the identifier comprises a signal generation circuit, wherein the signal generation circuit comprises a voltage controlled oscillator (VCO) and a digital control circuit coupled to the VCO, the digital control circuit assigned an address, the digital control circuit to control the VCO with a control signal associated with the address;

wherein the digital control circuit further comprises:
a digital counter circuit comprising an input portion coupled to the VCO and an output portion, wherein the VCO is operative to generate a first clock signal and a second clock signal, wherein the second clock signal is an inverted version of the first clock signal, and wherein the first and second clock signals are coupled to the digital counter circuit, wherein the digital counter circuit is operative to count a number of clock cycles received from the VCO, store the count in at least one register, and provide the count to the output portion of the digital counter circuit.

24. The in-body device according to claim 23, wherein the in-body device is an ingestible device.

25. The in-body device according to claim 23, wherein the in-body device is an implantable device.

26. The ingestible event marker according to claim 1, wherein the VCO is operative to generate a digital clock signal in response to activation of the identifier.

27. The ingestible event marker according to claim 1, wherein the control signal received by the VCO is encoded in a serial bit stream.

28. The ingestible event marker according to claim 1,
wherein the digital control circuit further comprises: a multiplexer circuit comprising an input portion and an output portion, the input portion of the multiplexer circuit is coupled to an output portion of the digital counter circuit, wherein the multiplexer circuit is operative to convert the count into an address stored in the multiplexer circuit.

29. The ingestible event marker according to claim 28, wherein the control signal produced by the multiplexer circuit encodes the address as a serial bit stream, wherein the control signal is provided to the VCO to control the output frequency of the VCO.

30. The ingestible event marker according to claim 29, wherein the digital control circuit further comprises:
an electrode drive circuit coupled to the multiplexer circuit to broadcast the serial bit stream which constitutes the address stored in the multiplexer circuit.

31. The system according to claim 16, wherein the VCO is operative to generate a digital clock signal in response to activation of the identifier.

32. The system according to claim 16, wherein the control signal received by the VCO is encoded in a serial bit stream.

33. The system according to claim 16,
wherein the digital control circuit further comprises:
a multiplexer circuit comprising an input portion and an output portion, the input portion of the multiplexer circuit coupled to an output portion of the digital counter circuit, wherein the multiplexer circuit is operative to convert the count into an address stored in the multiplexer circuit.

34. The system according to claim 33, wherein the control signal produced by the multiplexer circuit encodes the address as a serial bit stream, wherein the control signal is provided to the VCO to control the output frequency of the VCO.

35. The system according to claim 34, wherein the digital control circuit further comprises:
an electrode drive circuit coupled to the multiplexer circuit to broadcast the serial bit stream which constitutes the address stored in the multiplexer circuit.

36. The kit according to claim 20, wherein the VCO is operative to generate a digital clock signal in response to activation of the identifier.

37. The kit according to claim 20, wherein the control signal received by the VCO is encoded in a serial bit stream.

38. The kit according to claim 20,
wherein the digital control circuit further comprises:
a multiplexer circuit comprising an input portion and an output portion, the input portion of the multiplexer circuit coupled to an output portion of the digital counter circuit, wherein the multiplexer circuit is operative to convert the count into a corresponding address stored in the multiplexer circuit.

39. The kit according to claim 38, wherein the control signal produced by the multiplexer circuit encodes the address as a serial bit stream, wherein the control signal is provided to the VCO to control the output frequency of the VCO.

40. The kit according to claim 39, wherein the digital control circuit further comprises:
an electrode drive circuit coupled to the multiplexer circuit to broadcast the serial bit stream which constitutes the address stored in the multiplexer circuit.

* * * * *

UNITED STATES PATENT AND TRADEMARK OFFICE
CERTIFICATE OF CORRECTION

| | | |
|---|---|---|
| PATENT NO. | : 8,115,618 B2 | Page 1 of 1 |
| APPLICATION NO. | : 12/126798 | |
| DATED | : February 14, 2012 | |
| INVENTOR(S) | : Robertson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this
Twelfth Day of June, 2012

David J. Kappos
*Director of the United States Patent and Trademark Office*